US012773580B2

(12) United States Patent
Peyman et al.

(10) Patent No.: US 12,773,580 B2
(45) Date of Patent: Oct. 27, 2026

(54) CANCER IMAGING METHODS AND CANCER TREATMENT METHODS USING THERMOTHERAPY AND DRUG DELIVERY

(71) Applicant: Cancer Rx, LLC, Sun City, AZ (US)

(72) Inventors: Gholam A. Peyman, Sun City, AZ (US); Michael Kolios, Toronto (CA); Celina Yang, Toronto (CA); Jahangir Tavakkoli, Toronto (CA); Elyas Shaswary, Toronto (CA); Hisham Assi, Toronto (CA); Joseph Carl Kumaradas, Toronto (CA)

(73) Assignee: Cancer Rx, LLC, Sun City, AZ (US)

( * ) Notice: Subject to any disclaimer, the term of this patent is extended or adjusted under 35 U.S.C. 154(b) by 0 days.

(21) Appl. No.: 18/731,323

(22) Filed: Jun. 2, 2024

(65) Prior Publication Data

US 2024/0316371 A1 Sep. 26, 2024

Related U.S. Application Data

(62) Division of application No. 17/489,655, filed on Sep. 29, 2021, now Pat. No. 11,998,765.

(Continued)

(51) Int. Cl.
*A61N 7/02* (2006.01)
*A61K 31/7048* (2006.01)

(Continued)

(52) U.S. Cl.
CPC ............ *A61N 7/02* (2013.01); *A61K 31/7048* (2013.01); *A61K 41/0033* (2013.01);

(Continued)

(58) Field of Classification Search
CPC ............ A61K 41/0028; A61K 41/0052; A61K 49/22; A61K 49/221; A61K 49/225;

(Continued)

(56) References Cited

U.S. PATENT DOCUMENTS

| | | | |
|---|---|---|---|
| 3,993,754 | A | 11/1976 | Rahman et al. |
| 4,235,871 | A | 11/1980 | Papahadjopoulos et al. |

(Continued)

OTHER PUBLICATIONS

Taylor et al., "Glycogen Synthase Kinase 3 Inactivation Drives T-bet-Mediated Downregulation of Co-receptor PD-1 to Enhance CD8+ Cytolytic T Cell Responses," Immunity, Feb. 16, 2016, vol. 44, No. 2, pp. 274-286.

(Continued)

*Primary Examiner* — Boniface N Nganga

(74) *Attorney, Agent, or Firm* — The Law Office of Patrick F. O'Reilly III, LLC

(57) ABSTRACT

Cancer imaging methods and cancer treatment methods using thermotherapy and drug delivery are disclosed herein. In one embodiment, the temperature of heated tissue is determined from radio-frequency data from an ultrasound transducer based upon a change in backscattered energy of acoustic harmonics. In another embodiment, a plurality of nanocarriers containing an anti-tumor medication are administered to a patient, and are excited in a first non-thermal ultrasound mode and/or a second thermal ultrasound mode using an ultrasound source. In yet another embodiment, a plurality of nanoparticles are administered to a patient, then at least some of the nanoparticles are heated along with tissue at a site of a tumor, and a photoacoustic imaging unit is used to determine a temperature of the heated tissue at the site of the tumor.

10 Claims, 14 Drawing Sheets
(8 of 14 Drawing Sheet(s) Filed in Color)

Side View Cross-sectional View

Related U.S. Application Data

(60) Provisional application No. 63/085,007, filed on Sep. 29, 2020.

(51) Int. Cl.
*A61K 41/00* (2020.01)
*A61N 5/06* (2006.01)
*A61N 5/067* (2006.01)
*A61N 7/00* (2006.01)
*A61B 5/00* (2006.01)

(52) U.S. Cl.
CPC .......... *A61K 41/0042* (2013.01); *A61N 5/062* (2013.01); *A61N 5/067* (2021.08); *A61B 5/0095* (2013.01); *A61N 2005/0627* (2013.01); *A61N 2007/0004* (2013.01); *A61N 2007/0082* (2013.01)

(58) Field of Classification Search
CPC ........ A61K 9/00; A61K 9/2081; A61K 31/00; A61K 31/70; A61K 39/00; A61K 39/0011; A61K 47/00; A61K 47/62; A61K 47/69; A61K 47/6925; A61K 51/1045; A61B 5/0095
See application file for complete search history.

(56) References Cited

U.S. PATENT DOCUMENTS

| | | | | |
|---|---|---|---|---|
| 4,522,803 | A | 6/1985 | Lenk et al. | |
| 4,586,512 | A | 5/1986 | Do-Huu et al. | |
| 4,620,546 | A | 11/1986 | Aida et al. | |
| 4,658,828 | A | 4/1987 | Dory | |
| 4,891,043 | A | 1/1990 | Zeimer et al. | |
| 5,094,854 | A | 3/1992 | Ogawa et al. | |
| 5,118,666 | A | 6/1992 | Habener | |
| 5,149,319 | A | 9/1992 | Unger | |
| 5,203,782 | A | 4/1993 | Gudov et al. | |
| 5,220,181 | A | 6/1993 | Kanal et al. | |
| 5,545,618 | A | 8/1996 | Buckley et al. | |
| 5,935,942 | A | 8/1999 | Zeimer | |
| 5,976,502 | A | 11/1999 | Khoobehi et al. | |
| 6,179,767 | B1 | 1/2001 | Ziegler et al. | |
| 6,197,022 | B1 | 3/2001 | Baker | |
| 6,248,727 | B1 | 6/2001 | Zeimer | |
| 6,552,053 | B2 | 4/2003 | Sun et al. | |
| 6,566,595 | B2 | 5/2003 | Suzuki et al. | |
| 6,583,111 | B1 | 6/2003 | DiMarchi et al. | |
| 6,641,553 | B1 | 11/2003 | Chee et al. | |
| 6,984,655 | B1 | 1/2006 | Mori et al. | |
| 7,638,139 | B2 | 12/2009 | Peyman | |
| 8,324,344 | B2 | 12/2012 | Kisiel | |
| 9,849,092 | B2 | 12/2017 | Peyman | |
| 10,136,820 | B2 | 11/2018 | Peyman | |
| 10,300,121 | B2 | 5/2019 | Peyman | |
| 11,433,260 | B2 | 9/2022 | Peyman | |
| 2002/0174743 | A1 | 11/2002 | Mukherjee et al. | |
| 2003/0014089 | A1 | 1/2003 | Chow et al. | |
| 2003/0022374 | A1 | 1/2003 | Greenbaum et al. | |
| 2004/0003839 | A1 | 1/2004 | Curtain | |
| 2005/0004625 | A1 | 1/2005 | Chow | |
| 2006/0173362 | A1 | 8/2006 | Toms et al. | |
| 2010/0185260 | A1 | 7/2010 | Olson | |
| 2010/0211146 | A1 | 8/2010 | Strowbridge et al. | |
| 2011/0270153 | A1 | 11/2011 | Olson | |
| 2011/0287035 | A1 | 11/2011 | Peyman | |
| 2012/0052560 | A1* | 3/2012 | Knight | G01N 35/1095 435/286.1 |
| 2012/0226139 | A1 | 9/2012 | Peyman | |
| 2012/0253180 | A1* | 10/2012 | Emelianov | A61B 8/12 600/424 |
| 2014/0358068 | A1* | 12/2014 | Almutairi | A61N 5/062 604/20 |
| 2015/0157713 | A1* | 6/2015 | Peyman | A61K 47/6929 600/407 |
| 2015/0202466 | A1 | 7/2015 | Gertner | |
| 2016/0022976 | A1 | 1/2016 | Peyman | |
| 2018/0133298 | A1 | 5/2018 | Peyman | |
| 2018/0289805 | A1 | 10/2018 | Peyman | |
| 2019/0091350 | A1 | 3/2019 | Peyman | |

OTHER PUBLICATIONS

Husseini el al., "Ultrasonic-Activated Micellar Drug Delivery for Cancer Treatment," J Pharm Sci, May 27, 2008, vol. 98, No. 3, pp. 795-811.
Kong et al., "Efficacy of Liposomes and Hyperthermia in a Human Tumor Xenograft Model: Importance of Triggered Drug Release," Cancer Research, Dec. 15, 2000, vol. 60, pp. 6950-6957.
Phenix et al., "High Intensity Focused Ultrasound Technology, Its Scope and Applications in Therapy and Drug Delivery," Journal of Pharmacy & Pharmaceutical Sciences, Mar. 31, 2014, vol. 17, No. 1, pp. 136-153.
PCT Form 210, International Search Report for PCT/US2018/054880, mailed on Jan. 9, 2019.
PCT Form 237, Written Opinion of the International Searching Authority for PCT/US2018/054880, mailed on Jan. 9, 2019.
Helfand et al. "A Genetic-Based Approach to Personalized Prostate Cancer Screening and Treatment." Curr Opin Urol., Jan. 2015, 25(1): pp. 1-11.
E. Shaswary, Y. Xu, J. Tavakkoli, Performance study of a new time-delay estimation algorithm in ultrasonic echo signals and ultrasound elastography, Ultrasonics. 69 (2016), pp. 11-18.
B.C. Giovanella, A.C. Morgan, U.S. Stehlin, L.J. Williams, Selective Lethal Effect of Supranormal Temperatures on Mouse Sarcoma Cells, Cancer Res. 33 (1973), pp. 2568-2578.
M.A. Lewis, R.M. Staruch, R. Chopra, Thermometry and ablation monitoring with ultrasound, Int. J. Hyperth. 31 (2015), pp. 163-181.
R.M. Arthur, W.L. Straube, J.W. Trobaugh, E.G. Moros, Non-invasive estimation of hyperthermia temperatures with ultrasound, Int. J. Hyperth. 21 (2005), pp. 589-600.
R.M. Arthur, W.L. Straube, J. Trobaugh, E.G. Moros, In vivo change in ultrasonic backscattered energy with temperature in motion-compensated images, Int. J. Hyperth. 24 (2008), pp. 389-398.
R.M. Arthur, D. Basu, Y. Guo, J.W. Trobaugh, E.G. Moros, 3-D in vitro estimation of temperature using the change in backscattered ultrasonic energy, IEEE Trans. Ultrason. Ferroelectr. Freq. Control. 57 (2010), pp. 1724-1733.
C. Simon, P. VanBaren, E. Ebbini, Two-dimensional temperature estimation using diagnostic ultrasound, IEEE Trans. Ultrason. Ferroelectr. Freq. Control. 45 (1998), pp. 1088-1099.
D. Liu, E.S. Ebbini, Real-time 2-D temperature imaging using ultrasound, IEEE Trans. Biomed. Eng. 57 (2010), pp. 12-16.
E.S. Ebbini, C. Simon, D. Liu, Real-time ultrasound thermography and thermometry [Life Sciences], IEEE Signal Process. Mag. 35 (2018), pp. 166-174.
K.W.A. Van Dongen, M.D. Verweij, A feasibility study for non-invasive thermometry using non-linear ultrasound, Int. J. Hyperth. 27 (2011), pp. 612-624.
B. Maraghechi, M.H. Hasani, M.C. Kolios, J. Tavakkoli, Temperature dependence of acoustic harmonics generated by nonlinear ultrasound wave propagation in water at various frequencies, J. Acoust. Soc. Am. 139 (2016), pp. 2475-2481.
B. Maraghechi, M.C. Kolios, J. Tavakkoli, Temperature dependence of acoustic harmonics generated by nonlinear ultrasound beam propagation in ex vivo tissue and tissue-mimicking phantoms, Int. J. Hyperth. 31 (2015), pp. 666-673.
M. Bayat, J.R. Ballard, E.S. Ebbini, In vivo ultrasound thermography in presence of temperature heterogeneity and natural motions, IEEE Trans. Biomed. Eng. 62 (2015), pp. 450-457.
B. Maraghechi, Feasibility of noninvasive thermometry in hyperthermia regime using harmonics generated by nonlinear ultrasound wave propagation, Ryerson University, 2016, pp. 1-130.
F. Butt, High performance computing for linear acoustic wave simulation, Ryerson University, 2011, pp. 1-127.

(56) References Cited

OTHER PUBLICATIONS

F. Butt, A. Abhari, J. Tavakkoli, An application of high performance computing to improve linear acoustic simulation, in: Spring Simul. Multi-Conference, Boston, Massachusetts, 2011: pp. 71-78.

* cited by examiner

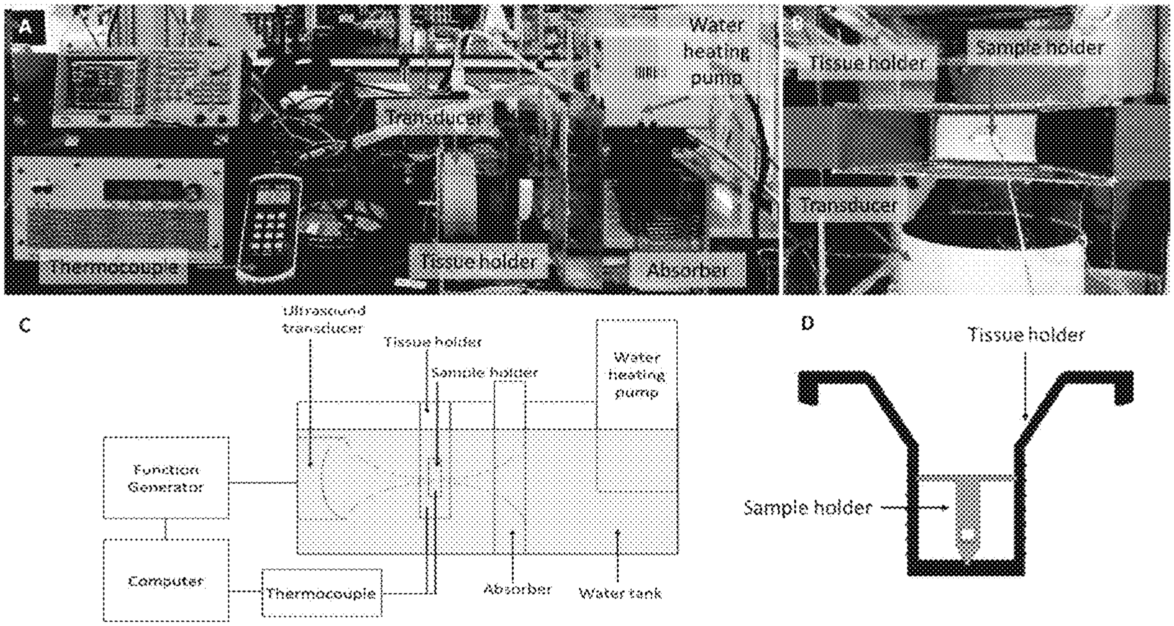

FIG. 14

Table 1: LIFU and pHIFU parameters for thermal and mechanical ultrasound exposures

| | LIFU exposure parameters for thermal treatment | pHIFU exposure parameters for mechanical treatment |
|---|---|---|
| Frequency | 1 MHz | 1 MHz |
| Single exposure time | 5 minutes with 50 % duty cycle | 25 ms pulse |
| Total exposure duration | 5 minutes | 30 s (25 ms pulse x 30 pulses at a rate of 1 pulse per second) |
| Input voltage | 160 mVpp | 500 mVpp |
| Output acoustic power | 2.1 W | 332 W |
| Focal peak positive pressure | 0.35 MPa | 3.3 MPa |
| Focal peak negative pressure | -0.30 MPa | -1.6 MPa |
| 6.0 °C | 0.5 °C | |

FIG. 15

CANCER IMAGING METHODS AND CANCER TREATMENT METHODS USING THERMOTHERAPY AND DRUG DELIVERY

CROSS-REFERENCE TO RELATED APPLICATIONS

This is a divisional of U.S. Nonprovisional patent application Ser. No. 17/489,655, entitled "Cancer Imaging Methods And Cancer Treatment Methods Using Thermotherapy And Drug Delivery", filed on Sep. 29, 2021; and U.S. application Ser. No. 17/489,655 claims priority to U.S. Provisional Patent Application No. 63/085,007, entitled "Cancer Imaging Methods And Cancer Treatment Methods Using Thermotherapy And Drug Delivery", filed on Sep. 29, 2020, the disclosure of each of which is hereby incorporated by reference as if set forth in their entirety herein.

INCORPORATION BY REFERENCE OF MATERIAL SUBMITTED ON A COMPACT DISK

Not Applicable.

BACKGROUND OF THE INVENTION

1. Field of the Invention

The invention generally relates to cancer imaging methods and cancer treatment methods using thermotherapy and drug delivery. More particularly, the invention relates to cancer imaging methods and cancer treatment methods using nanoparticles and photoacoustics, ultrasound, laser, and/or an alternating magnetic field for thermotherapy and drug delivery.

2. Background

A real-time and non-invasive thermometry technique is essential in thermal therapies to monitor and control the treatment. The current clinical standard for temperature measurement in the body is performed by either temperature sensing probes or magnetic resonance imaging (MRI). However, temperature sensing probes are invasive and provide a temperature measurement only at a single point and MRI systems are expensive and require MRI-compatible heating modalities. Ultrasound (US) is an attractive thermometry modality due to its relatively high sensitivity to change in temperature and fast data acquisition and processing capabilities. In addition, US thermometry is inexpensive, portable and non-ionizing. For US thermometry, a temperature sensitive acoustic parameter is required to track the changes in that parameter during the treatment. Among existing US thermometry methods, the backscattered RF echo-shift is currently the most established one and its feasibility has been demonstrated in a small animal model in vivo. However, the echo-shift method is highly sensitive to tissue motion (mainly respiratory and cardiac motion). In addition, this method suffers from erroneous temperature estimates in the distal area to the heated region due to the distortion of the US beam as they traverse the region undergoing temperature change.

The echo-shift technique estimates the temperature change in a uniform medium as:

$$\delta T(z) = \frac{c_0}{2}\left(\frac{1}{\alpha - \lambda}\right)\frac{d}{dz}(\delta t(z)), \tag{1}$$

where $c_0$ is the SOS at the initial temperature, $\alpha=(\partial d(T)/\partial T)/d(T)$ is the linear coefficient of thermal expansion of the medium, $\lambda=(\partial c(T)/\partial T)/c(T)$ is the thermal coefficient of the SOS, and $\delta t(z)$ is the cumulative time-shift at depth z. The first term in Eq. (1), $$\frac{c_0}{2}\left(\frac{1}{\alpha - \lambda}\right),$$

is a material-dependent parameter denoted by k, and the second term, $$\frac{d}{dz}(\delta t(z)),$$

is the axial gradient of the cumulative shifts in the RF echo signal.

Therefore, what is needed is an US thermometry method that is less susceptible to tissue motion. In addition, an US thermometry method is needed that is more sensitive to temperature compared to the echo-shift method.

Moreover, chemotherapy is a primary curative modality for many types of cancers. It involves administering pharmaceutical compounds that exert cytotoxic effects and disrupt the rapid overgrowth of malignant cells. However, the side effects of the chemotherapeutic agents caused by poor drug distribution and lack of confinement to the target region remain a problem.

Nanocarriers, such as liposomes, are used to overcome the issues with conventional chemotherapeutic agents. Liposomes are spherical bilayer vesicles that are composed of phospholipid membranes and an aqueous core and are used as carriers for molecules. Liposomes are the most studied nanoparticle-based drug delivery systems for cancer treatment. Liposomes are generally biocompatible, and liposome-based drug delivery has several advantages compared to the administration of the free drug. Advantages include: (a) an increase in drug accumulation in the tumour tissue due to the enhanced permeability and retention (EPR) effect and (b) confining the cytotoxic molecules within a non-toxic carrier. This approach can minimize normal tissue exposure to the cytotoxic agents by selective focused ultrasound exposure. However, passive drug accumulation from the EPR effect can take days to achieve maximum effect, and the encapsulation of the drug can also limit the timely release and uptake of the drugs at the tumour site. Liposome systems that respond to external stimuli such as temperature, pH, electromagnetic fields, ultrasound, and light have been studied to overcome the limitations of timely release. Among the different stimuli, ultrasound poses an advantage as it can propagate into deep tissues as long as there is an acoustic path for the ultrasound to travel through.

The mechanism of drug release with ultrasound can broadly be divided into thermal and mechanical processes (or a combination of both). The thermal release requires an ultrasound-induced temperature increase at the target region from the absorption of acoustic energy. The thermal release using ultrasound generally requires moderate intensities of several W/cm$^2$, high duty cycles up to 100%, moderate pressures of 100 s of kPa to MPa range, and long treatment times, of the order of several seconds to 30 minutes. High-intensity focused ultrasound (HIFU) has a focal intensity of a few kW/cm$^2$' and the temperature rise is 60-100° C. HIFU therapy is used to damage diseased tissue through ablation or cavitation. Low-intensity focused ultrasound has a focal intensity of a few tens of $W/cm^2$ and results in the temperature rise of 41-45° C.

Therefore, what is needed is a method for releasing a drug from nanocarriers using both thermal and mechanical ultrasound processes. In addition, a method is needed for measuring the release of the drug from the nanocarriers using the thermal and mechanical ultrasound processes.

Furthermore, thermal therapy is currently used either as a stand-alone cancer treatment or in combination with other treatment modalities, such as radiation therapy, chemotherapy, and heat-activated drug release using thermosensitive liposomes. Despite the successful clinical application of some of these modalities, a major limitation remains the lack of simple real-time non-invasive thermal imaging for adaptive localization and control of the temperature.

The monitoring and control of temperature rise in a malignant lesion are imperative for assuring that the prescribed temperature is delivered to the tumour for a desired time while protecting the vital tissue and organs surrounding it. The current standard for temperature measurement and control during thermal therapy is either point temperature sensors or magnetic resonance thermal imaging (MRTI). The former is invasive and only provides spatially sparse thermometry while the latter is both expensive and requires MRI compatible equipment. Hence, there is a need for inexpensive and non-invasive temperature monitoring. Some of the emerging non-invasive thermometry methods that meet these needs are ultrasound (US) and photoacoustic (PA) thermometry.

Photoacoustic (PA) imaging is an emerging hybrid modality that has the contrast of optical imaging and the high resolution of ultrasound imaging. Nanosecond pulses of light illuminate the area of interest resulting in small rapid temperature increases due to light absorption, causing a subsequent thermoelastic expansion in the medium that produces acoustic waves that are measured at the surface of the imaged tissue using a US transducer. PA imaging, therefore, produces an image of optical absorbers distribution, making it complementary to US imaging, which produces an image of acoustic scatterers. The ability of photoacoustic imaging to provide structural and functional imaging has led to attempts to use it in diverse application areas, including temperature monitoring in tissues. For hyperthermia where heating does not induce significant changes in the tissue's optical properties, the heating-induced change of the PA emission depends mainly on the change in the Gruneisen parameter. Photoacoustic thermometry has resulted in encouraging outcomes using tissue phantoms, and recently, in some in-vivo studies. Nevertheless, improvements are still needed, especially in producing sufficient quality temperature images for reliable real-time non-invasive monitoring and control of temperature.

BRIEF SUMMARY OF EMBODIMENTS OF THE INVENTION

Accordingly, the present invention is directed to cancer imaging methods and cancer treatment methods using thermotherapy and drug delivery that substantially obviate one or more problems resulting from the limitations and deficiencies of the related art.

In accordance with one or more embodiments of the present invention, there is provided a non-invasive thermometry method for use in cancer treatment and/or imaging. The method comprises the steps of: (i) heating tissue using a thermal energy source at a site of a tumor so as to damage one or more tumor cell membranes and release antigenic material in vivo that activates and stimulates an immunogenic response of the patient at the site of the tumor; (ii) imaging the heated tissue at the site of the tumor using an imaging ultrasound transducer so as to acquire radio-frequency data; and (iii) determining, by using an ultrasound scanner, a temperature of the heated tissue at the site of the tumor from the radio-frequency data acquired by the imaging ultrasound transducer, the temperature being determined from the radio-frequency data based upon a change in backscattered energy of acoustic harmonics.

In a further embodiment of the present invention, the thermal energy source for heating the tissue is selected from the group consisting of ultrasound, laser, an alternating magnetic field, microwave radiation, and radiofrequency (RF) energy.

In yet a further embodiment, the thermal energy source for heating the tissue is a therapeutic ultrasound transducer operating in a low intensity focused ultrasound (LIFU) mode.

In still a further embodiment, the therapeutic ultrasound transducer has a central frequency of approximately 1 megaHertz; and the step of heating the tissue further comprises heating the tissue to a temperature in a range between about 37° C. and about 47° C. using an acoustic power of approximately 4.5 watts, a frequency of approximately 1 megaHertz, and a 50% duty cycle.

In yet a further embodiment, the imaging ultrasound transducer is a linear array-type transducer with a central frequency of approximately 4.2 megaHertz and a sampling rate of 31.25 megaHertz.

In still a further embodiment, the step of determining the temperature of the heated tissue further comprises determining, by using the ultrasound scanner, two-dimensional temperature maps of the heated tissue from the radio-frequency data.

In yet a further embodiment, the step of determining the temperature of the heated tissue further comprises determining, by using the ultrasound scanner, the temperature from the radio-frequency data based upon a change in backscattered energy of the fundamental acoustic harmonic ($BE_{f0}$) and second acoustic harmonic ($BE_{h2}$).

In accordance with one or more other embodiments of the present invention, there is provided a cancer treatment method using ultrasound energy for targeted drug delivery. The method comprises the steps of: (i) administering a plurality of nanocarriers to a patient in need thereof so as to target a tumor in the patient, the administered nanocarriers containing an anti-tumor medication; and (ii) exciting the nanocarriers in a first non-thermal ultrasound mode and/or a second thermal ultrasound mode using an ultrasound source that generates a non-thermal ultrasonic wave and/or a thermal ultrasonic wave so as to release the anti-tumor medication from one or more of the plurality of nanocarriers at a site of the tumor.

In a further embodiment of the present invention, the plurality of nanocarriers are selected from the group consisting of antibody-conjugated nanoparticles, aptamer-conjugated nanoparticles, liposomes, and micelles.

In yet a further embodiment, at least some of the plurality of nanocarriers are conjugated with cell penetrating peptides (CPPs).

In still a further embodiment, the ultrasound source is a therapeutic ultrasound transducer with a frequency of approximately 1 megaHertz.

In yet a further embodiment, the step of exciting the nanocarriers further comprises exciting the nanocarriers using the therapeutic ultrasound transducer in the first non-thermal ultrasound mode, the therapeutic ultrasound transducer emitting pulsed high intensity focused ultrasound (pHIFU) for mechanical excitation of the plurality of nanocarriers in the first non-thermal ultrasound mode so as to release the anti-tumor medication from the nanocarriers by rupturing membranes of the nanocarriers and/or peeling a polymer coating off the nanocarriers.

In still a further embodiment, the step of exciting the nanocarriers with the pulsed high intensity focused ultrasound (pHIFU) in the first non-thermal ultrasound mode further comprises generating approximately 25 millisecond pulses at a pulse repetition frequency of approximately 1 Hertz with a focal peak pressure of approximately 3.3 megapascals for a total exposure time duration of approximately 30 seconds.

In yet a further embodiment, in the first non-thermal ultrasound mode where the therapeutic ultrasound transducer is emitting the pulsed high intensity focused ultrasound (pHIFU), the therapeutic ultrasound transducer has an acoustic power of approximately 332 watts and an input voltage of approximately 500 mVpp.

In still a further embodiment, the step of exciting the nanocarriers further comprises exciting the nanocarriers using the therapeutic ultrasound transducer in the second thermal ultrasound mode, the therapeutic ultrasound transducer emitting low intensity focused ultrasound (LIFU) for thermal heating of the plurality of nanocarriers in the second thermal ultrasound mode so as to release the anti-tumor medication from the nanocarriers by thermally rupturing the nanocarriers and/or melting a polymer coating of the nanocarriers.

In yet a further embodiment, the step of exciting the nanocarriers with the low intensity focused ultrasound (LIFU) in the second thermal ultrasound mode further comprises generating a thermal ultrasonic wave with a frequency of approximately 1 megaHertz at a focal peak pressure of approximately 0.35 megapascals and a 50% duty cycle for a total exposure time duration of approximately 5 minutes.

In still a further embodiment, in the second thermal ultrasound mode where the therapeutic ultrasound transducer is emitting the low intensity focused ultrasound (LIFU), the therapeutic ultrasound transducer has an acoustic power of approximately 2.1 watts and an input voltage of approximately 160 mVpp.

In yet a further embodiment, in the second thermal ultrasound mode where the therapeutic ultrasound transducer is emitting the low intensity focused ultrasound (LIFU), the therapeutic ultrasound transducer thermally heats the plurality of nanocarriers to a temperature in a range between about 37° C. and about 47° C. under feedback control of the therapeutic ultrasound transducer by a feedback controller.

In still a further embodiment, the anti-tumor medication comprises doxorubicin.

In accordance with yet one or more other embodiments of the present invention, there is provided a cancer treatment method using nanoparticle-mediated thermal therapy using photoacoustic imaging. The method comprising the steps of: (i) administering a plurality of nanoparticles to tissue at a site of a tumor in a patient; (ii) heating the tissue and at least some of the plurality of nanoparticles at the site of the tumor using a thermal energy source so as to generate photoacoustic signals, damage one or more tumor cell membranes, and release antigenic material in vivo that activates and stimulates an immunogenic response of the patient at the site of the tumor; (iii) performing photoacoustic imaging with a photoacoustic imaging unit so as to acquire the photoacoustic signals; and (iv) determining, by using the photoacoustic imaging unit, a temperature of the heated tissue at the site of the tumor from the photoacoustic signals.

In a further embodiment of the present invention, the cancer treatment method further comprises a proportional-integral-derivative (PID) controller operatively coupled to the thermal energy source and the photoacoustic imaging unit; and the step of heating the tissue and the at least some of the plurality of nanoparticles at the site of the tumor further comprises controlling the thermal energy source using the proportional-integral-derivative (PID) controller based on the temperature determined by the photoacoustic imaging unit in order to heat the tissue and the at least some of the plurality of nanoparticles to a prescribed temperature so as to provide real-time control of nanoparticle-mediated thermal therapy.

In yet a further embodiment, the thermal energy source for heating the tissue is selected from the group consisting of laser, ultrasound, an alternating magnetic field, microwave radiation, and radiofrequency (RF) energy.

In still a further embodiment, the photoacoustic imaging unit comprises an ultrasound transducer and a nanosecond excitation laser.

In yet a further embodiment, the ultrasound transducer of the photoacoustic imaging unit operates a frequency of approximately 21 megaHertz and the nanosecond excitation laser operates in a wavelength range of about 680 nanometers to about 930 nanometers.

In still a further embodiment, a first subset of the plurality of nanoparticles administered to the tissue at the site of the tumor in the patient comprises gold nanoparticles; and the step of heating the tissue and the at least some of the plurality of nanoparticles further comprises heating at least some of the gold nanoparticles at the site of the tumor, the heating of the gold nanoparticles resulting in an increased temperature rise at the site of the tumor that is five to seven times greater than a temperature rise achieved without the administration of gold nanoparticles.

In yet a further embodiment, a second subset of the plurality of nanoparticles administered to the tissue at the site of the tumor in the patient comprises liposomes containing an anti-tumor medication.

In still a further embodiment, the anti-tumor medication comprises doxorubicin.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The invention will now be described, by way of example, with reference to the accompanying drawings, in which.

side (b) cross-sectional views, wherein the field was generated using linear acoustic and temperature simulator (LATS).

Figure 3:
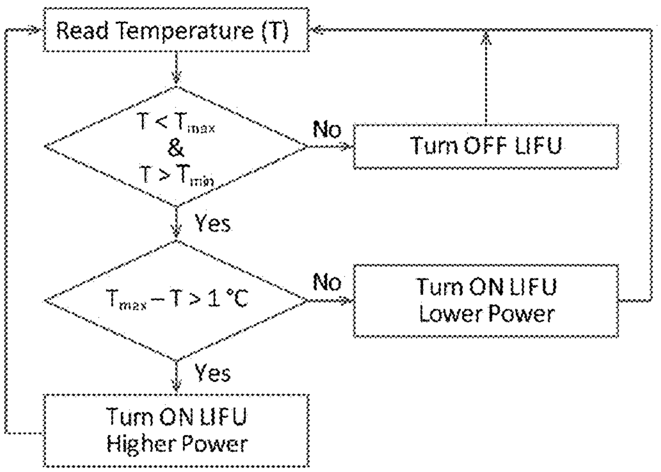

FIG. 3 is a block diagram of the temperature control LIFU system, according to one embodiment of the invention, where $T_{max}$ and $T_{min}$ were the upper and lower tolerance of the target temperature.

Figure 4:
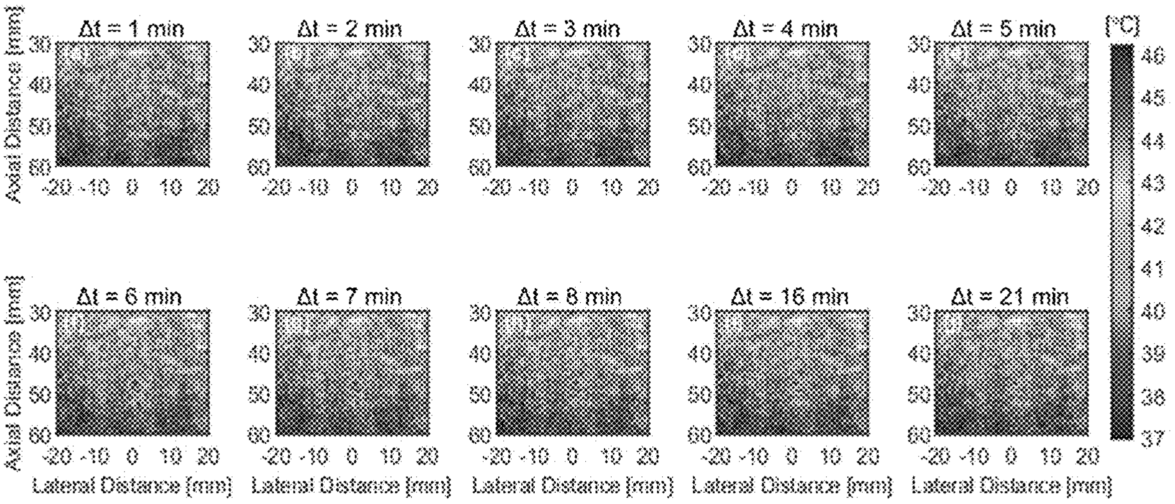

FIG. 4 illustrates temperature maps of the 2nd harmonic CBE($CBE_{h2}$). The baseline temperature was 37° C. The tissue was exposed to LIFU for 6 minutes. In (a)-(f) the tissue was being heated and in (g)-(j) the tissue was being let to return to baseline temperature. The focal region of the therapeutic transducer was at the point with coordinates of 47 mm axial and 0 mm lateral.

Figure 5:
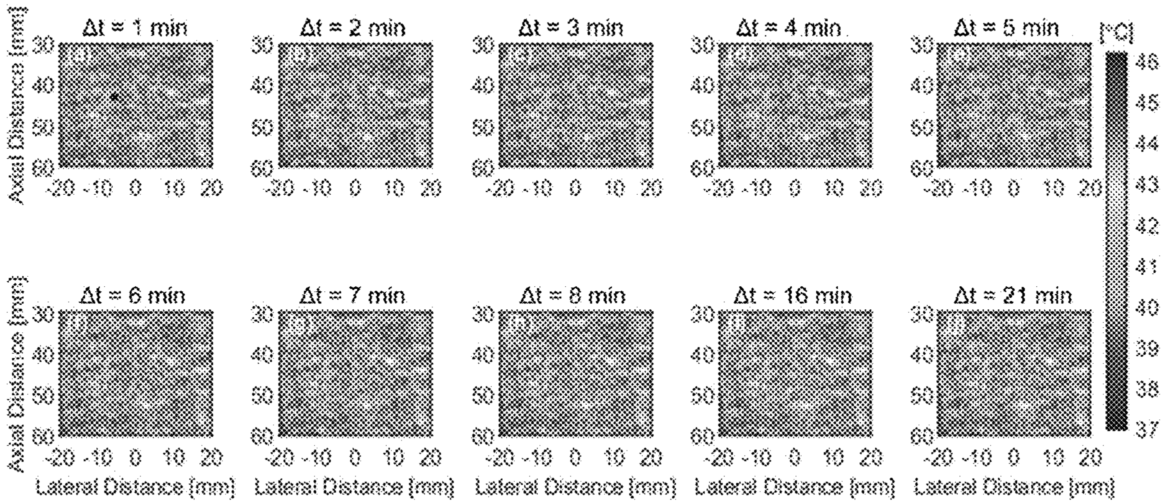

FIG. 5 illustrates temperature maps of the combined CBE($CBE_{comb}$). The baseline temperature was 37° C. The tissue was exposed to LIFU for 6 minutes. In (a)-(f) the tissue was being heated and in (g)-(j) the tissue was being let to return to baseline temperature. The focal region of the therapeutic transducer was at the point with coordinates of 47 mm axial and 0 mm lateral.

Figure 6:
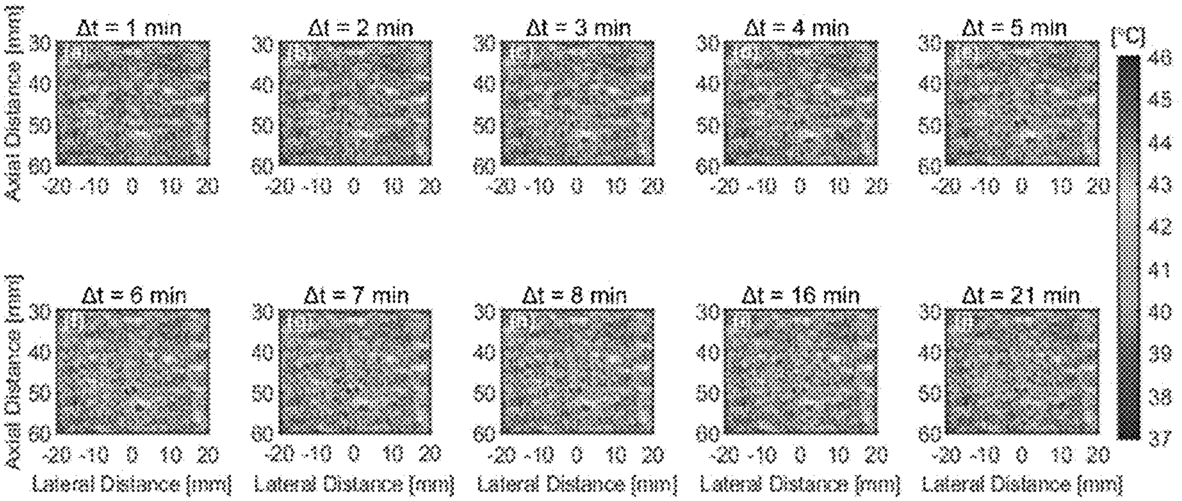

FIG. 6 illustrates temperature maps using the echo-shift method. The baseline temperature was 37° C. The tissue was exposed to LIFU for 6 minutes. In (a)-(f) the tissue was being heated and in (g)-(j) the tissue was being let to return to baseline temperature. The focal region of the therapeutic transducer was at the point with coordinates of 47 mm axial and 0 mm lateral.

Figure 7:
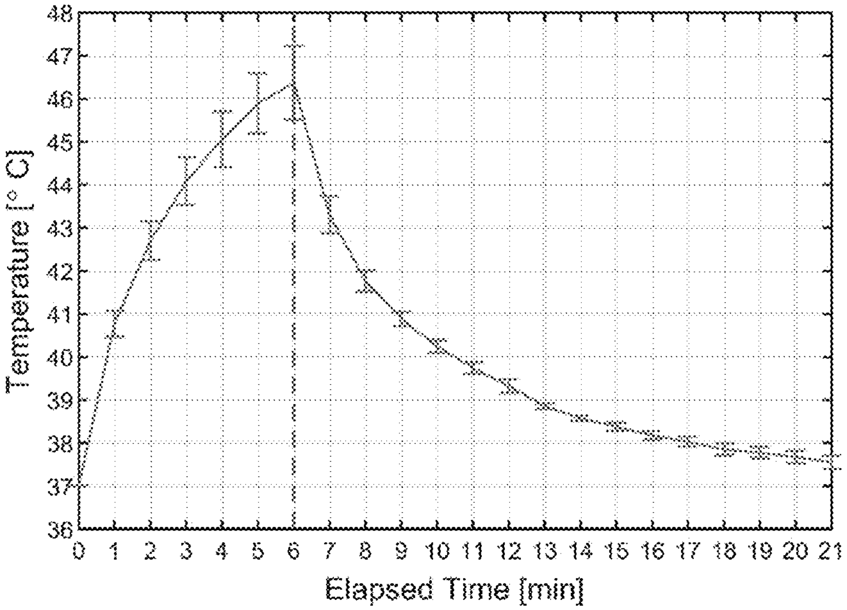

FIG. 7 illustrates a temperature reading from the thermocouple. The tissue was exposed to LIFU for 6 minutes. Average of 5 different trials with different tissue samples is shown. The error bars represent standard error.

Figure 8:
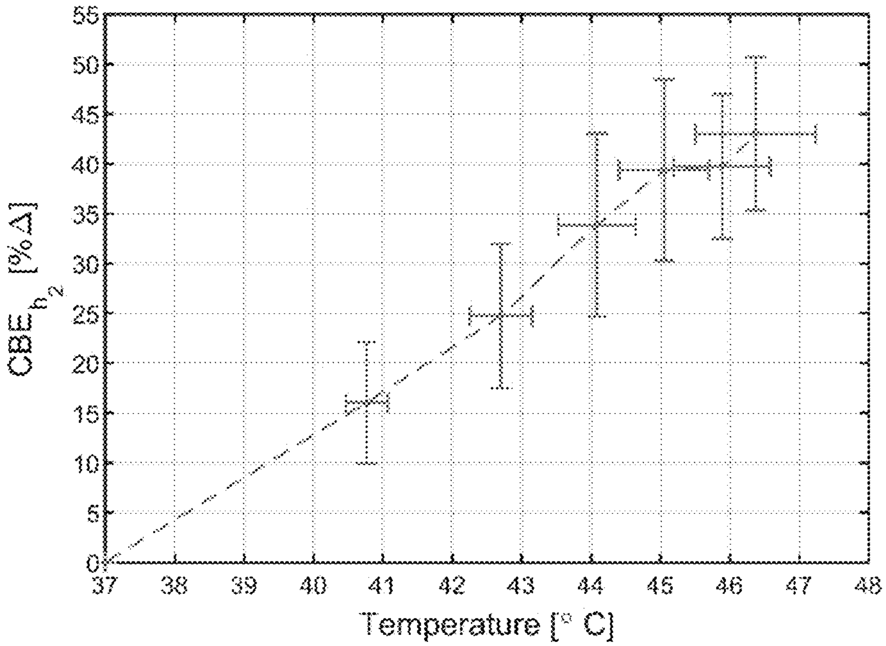

FIG. 8 illustrates the average percentage change in $CBE_{h2}$ as a function of temperature. The error bars represent standard error of 5 trials.

Figure 9:
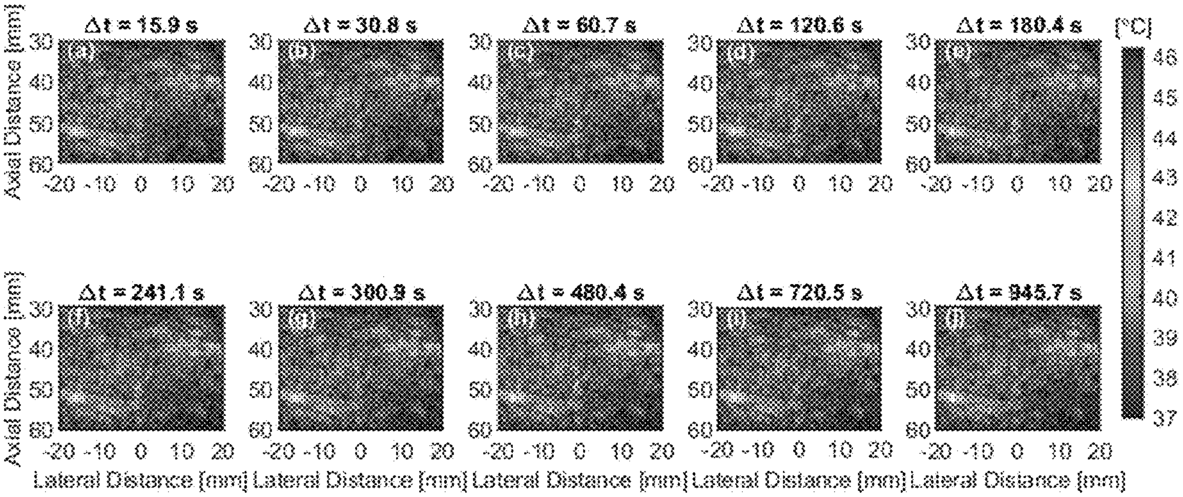

FIG. 9 illustrates temperature maps of the $CBE_{comb}$. The baseline temperature was 37° C. The temperature at the focal region was controlled for 4 minutes using pre-determined duty cycle and amplitude for the therapeutic transducer to maintain the temperature at 43° C. After 4 minutes, the ex vivo tissue was let to naturally cool down. The focal region of the therapeutic transducer was at the point with coordinates of 48 mm axial and 0 mm lateral.

Figure 10:
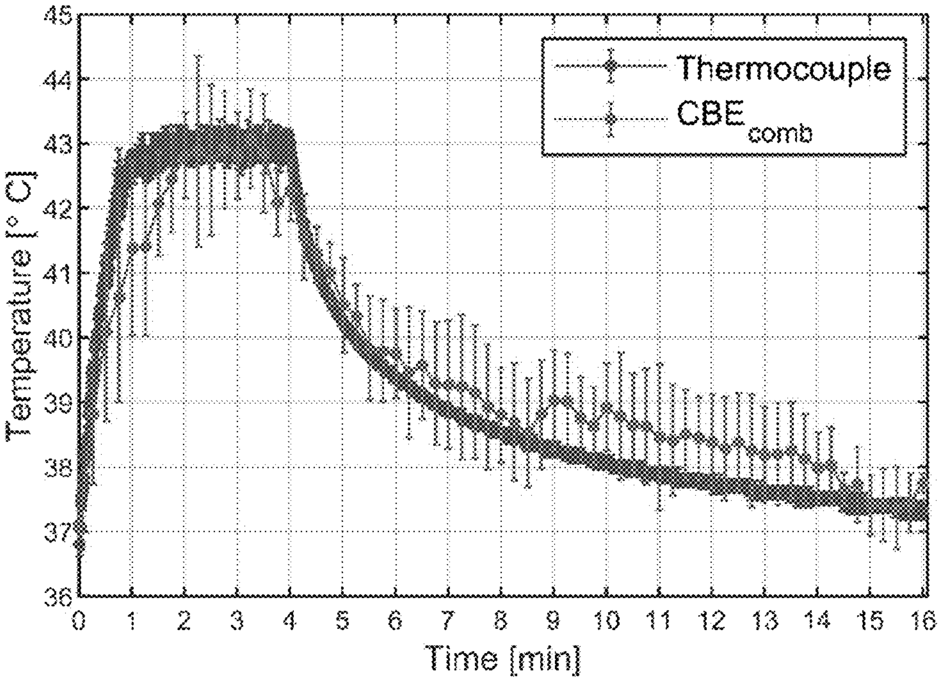

FIG. 10 illustrates the average temperature measured by a calibrated needle thermocouple (n=3) and calculated by the $CBE_{comb}$ method (n=4). The error bars represent standard deviation.

Figure 11:
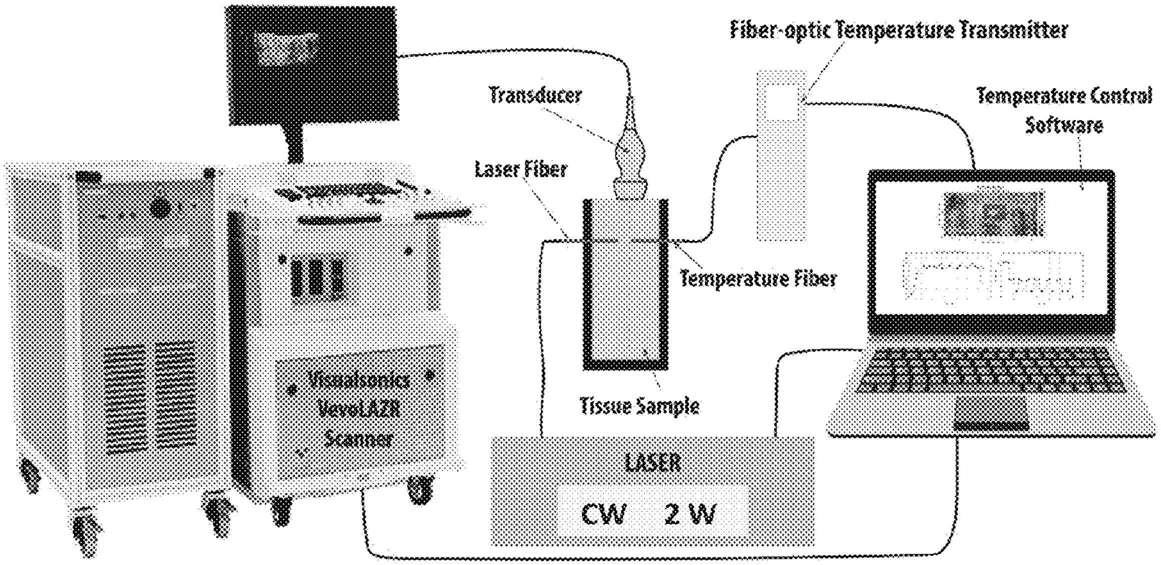

FIG. 11 is a schematic diagram of another experimental setup for an ultrasound thermometry method, according to another embodiment of the invention.

Figure 12:
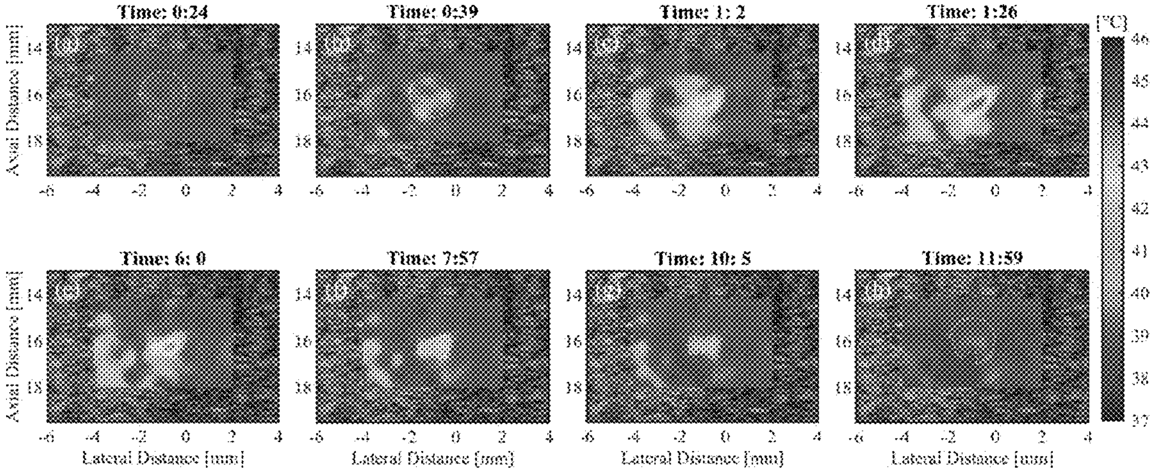

FIG. 12 illustrates temperature maps generated using the CBE method overlaid on the B-mode image at various times in ex vivo tissue samples. The baseline temperature was 37° C. The temperature at about 2 mm away from the laser heating fiber was controlled for 6 minutes by a closed-loop temperature controller in real-time. After 6 minutes the laser was turned off and the ex vivo tissue sample was let to naturally cool down. The dotted lines show the region where the average temperature was estimated. Time format is shown in minutes:seconds.

Figure 13:
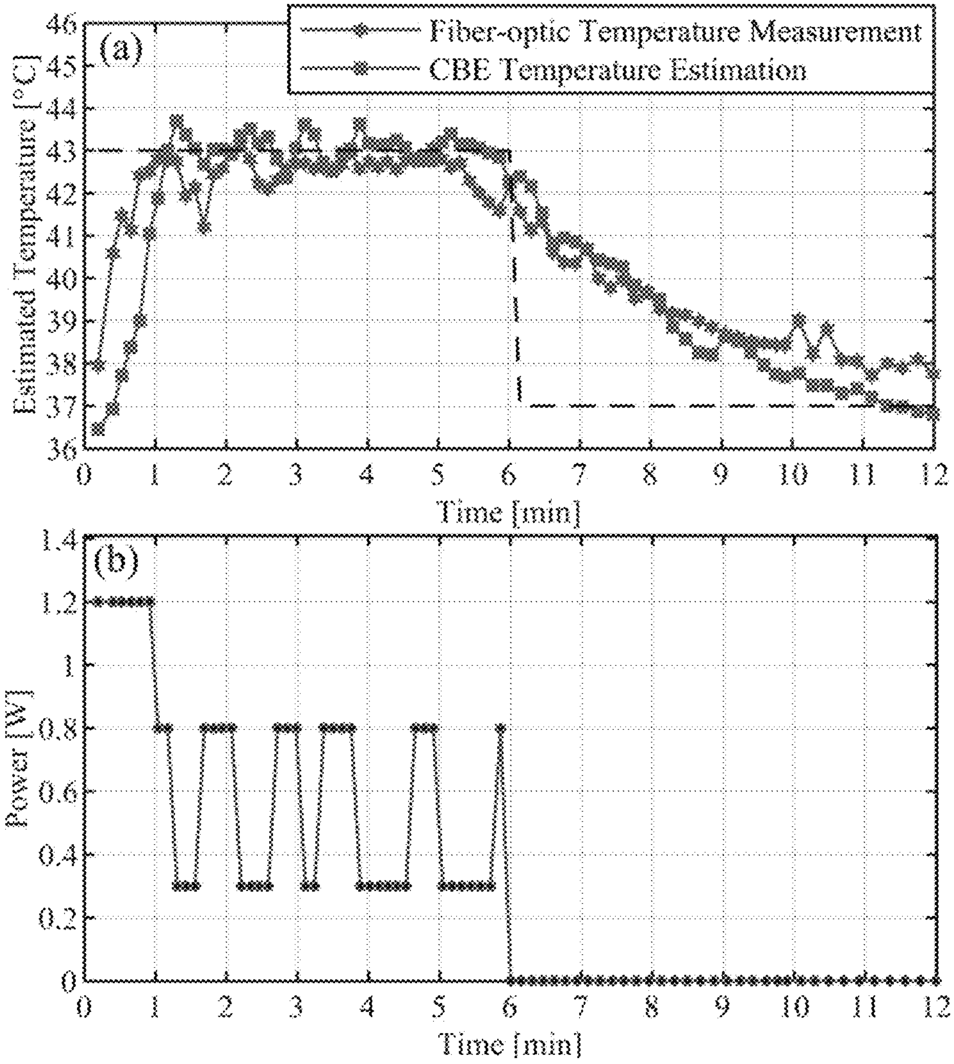

FIG. 13 illustrates a first graph (a) of the average temperature in the region of interest estimated by the CBE temperature maps and measured by the fiber-optic temperature sensor as a function of time, and a second graph (b) of the laser power being controlled by the temperature controller as a function of time.

FIG. 14 illustrates the setup to determine the release of doxorubicin from thermosensitive liposomes with intensive focused ultrasound exposures (A) side view; (B) top view; (C) schematic; (D) schematic of the 3D printed tissue holder ($3\times8\times5$ $cm^3$) and sample holder (loading dimensions of $0.5\times1\times1$ $cm^3$).

FIG. 15 illustrates a table of low intensity focused ultrasound (LIFU) and pulsed high intensity focused ultrasound (pHIFU) parameters for thermal and mechanical ultrasound exposures.

Figure 16:
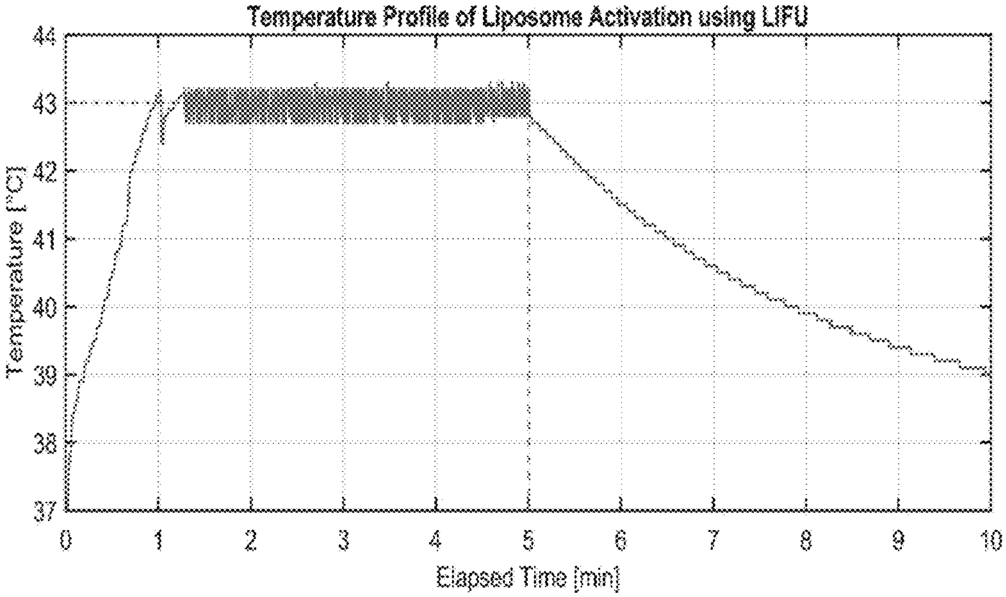

FIG. 16 illustrates a representative temperature profile of liposomes with controlled LIFU. The dotted lines represent the prescribed temperature (43° C.) and time period (5 min). The cool-down temperature profile is also recorded for another 5 min after the LIFU has been turned off.

Figure 17:
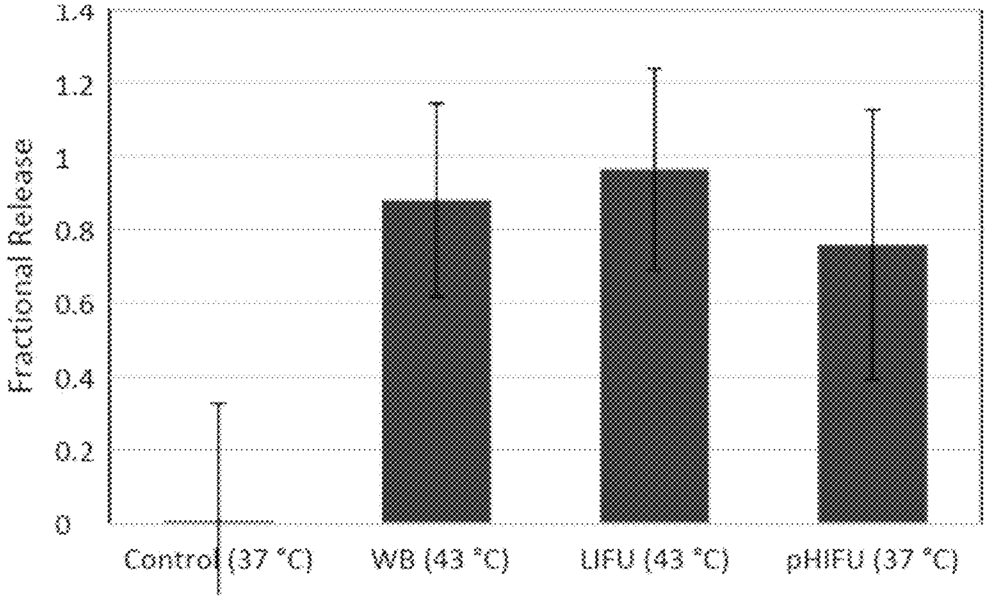

FIG. 17 illustrates a fractional release of doxorubicin-loaded in liposomes of control, water bath heated, heated with LIFU, and pHIFU exposed samples. The control, WB (43° C.), LIFU (43° C.) are the mean of five independent experiments, and the pHIFU (37° C.) is the mean of three independent experiments. The error bars represent the standard deviation.

Figure 18:
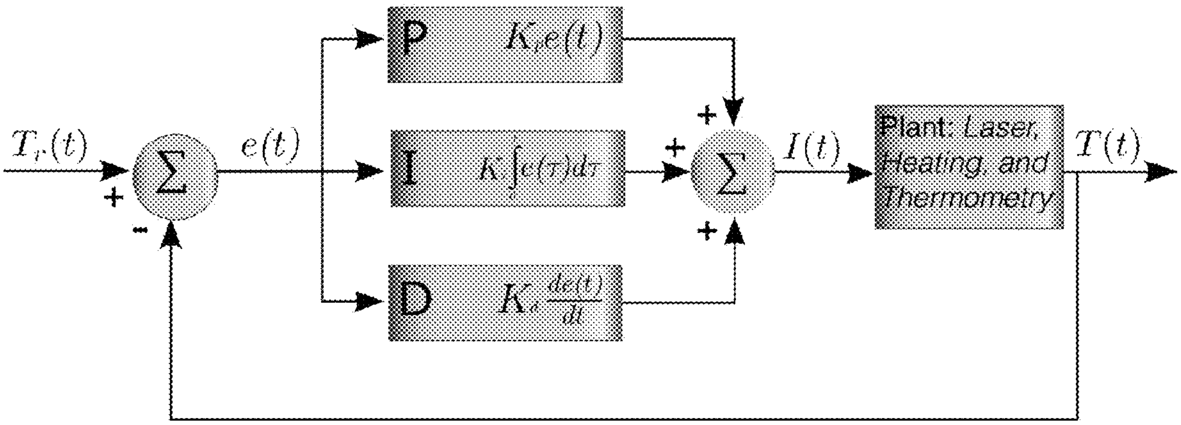

FIG. 18 illustrates a schematic of a PID controller for the laser thermal therapy treatment, according to one embodiment of the invention. The error value, e(t), between the targeted reference temperature, Tr (t), and the measured temperature, T (t), along with the integral and the derivative of this error value are used to predict the control variable I(t). In laser thermal therapy, the control variable could be the current that drives the laser power or the laser power itself.

Figure 19:
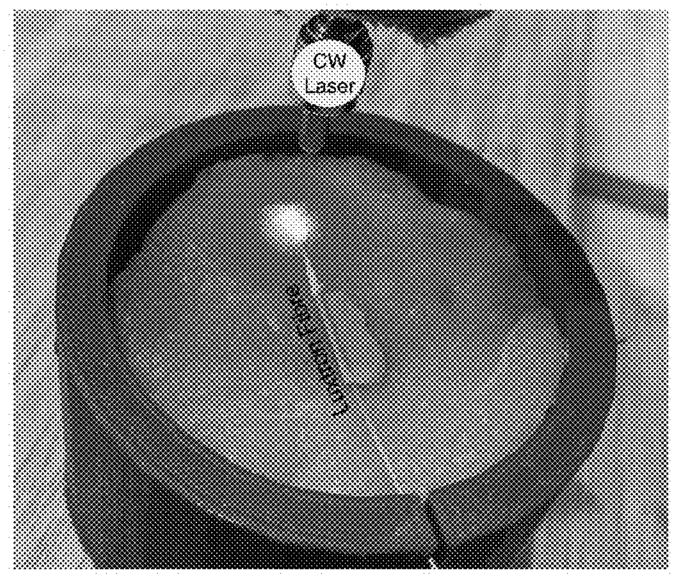

FIG. 19 illustrates a surface heating experimental setup. Pork loin tissue is placed in a holder under irradiation from an 808 nm CW laser fibre. The red light in the figure is a marking light. The temperature is recorded using a fluoroptic thermometry fibre.

Figure 20:
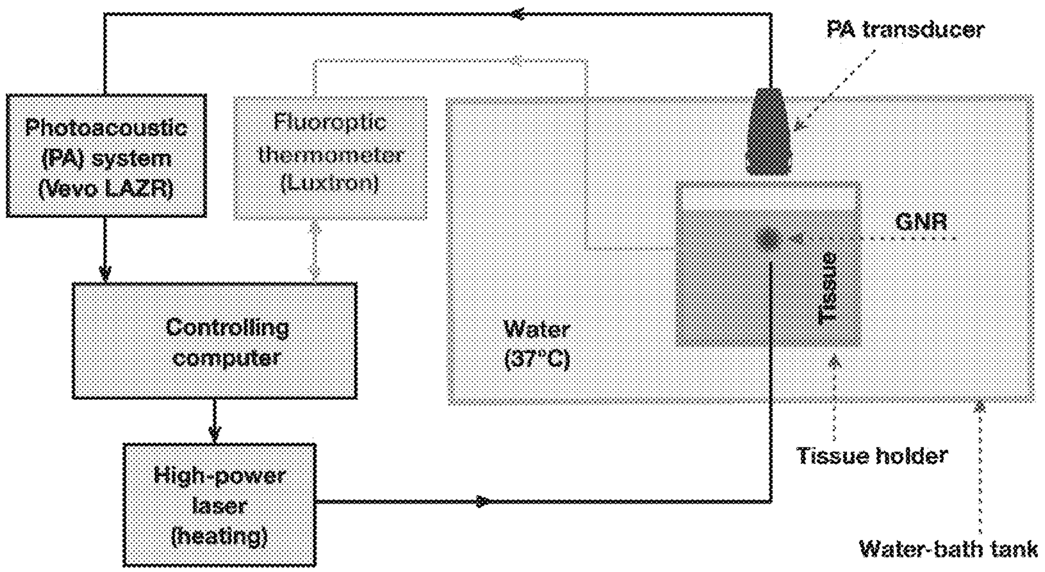

FIG. 20 illustrates a schematic diagram of the ex-vivo experimental setup of PA thermometry and laser thermal therapy based on it, according to one embodiment of the invention.

Figure 21:
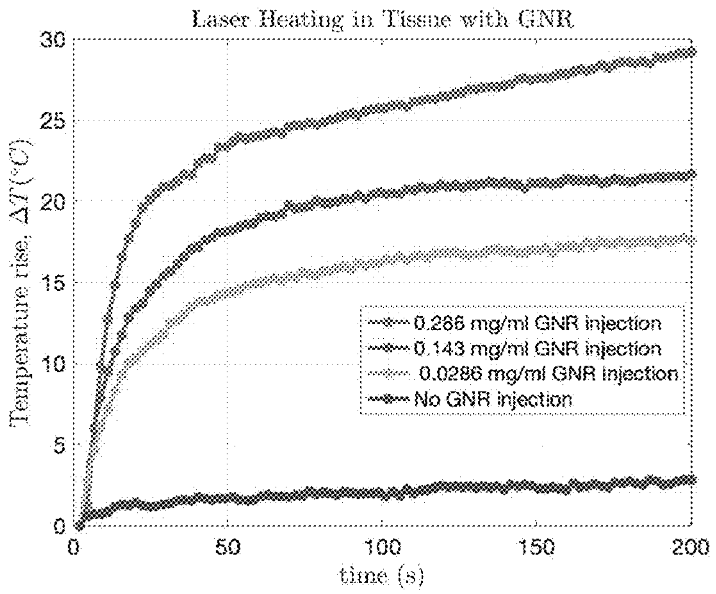

FIG. 21 illustrates the effect of GNRs at various concentrations on laser-induced heating at a tissue surface. The surface heating experimental setup shown in FIG. 19 was used. The bottom curve shows the temperature rise due to the irradiation of 500 mW laser without any GNR being injected. The other three curves show the temperature rise when GNR, with three different concentrations of GNRs are injected into the surface.

Figure 22:
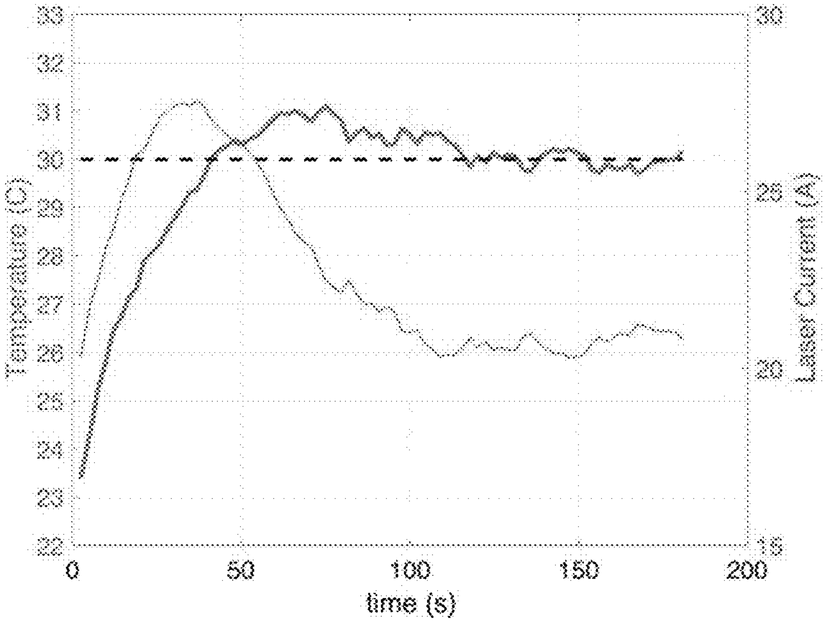

FIG. 22 illustrates graphical results from a controlled surface laser heating experiment. The tissue is initially at room temperature (around 23° C.), with a targeted temperature of 30° C. (7° C. increase) for three minutes. The dashed line represents the prescribed targeted temperature, the bolder curve represents the actual measured temperature, while the less bold curve represents the laser current. The steady-state mean absolute deviation (MAD) from the targeted temperature is 0.36° C. The PID coefficients used in this experiment are Kp=1.2, Ki=0.15, and Kd=0.01.

Figure 23:
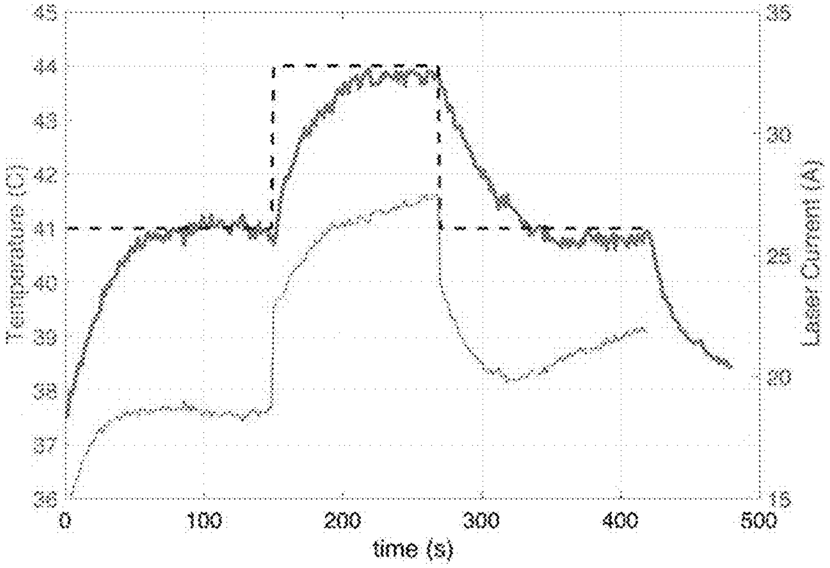

FIG. 23 illustrates graphical results from a controlled laser heating treatment with three prescribed stages; two and half minutes at 41° C., then two minutes 44° C., and back to 41° C. for two and a half minutes. The dashed line represents the prescribed targeted temperature, the top curve represent the actual measured temperature, and the bottom curve represents the value of the current that controls the laser power based on the PID controller. The steady-state mean absolute deviation (MAD) from the targeted temperature is 0.16° C.

Figure 24:
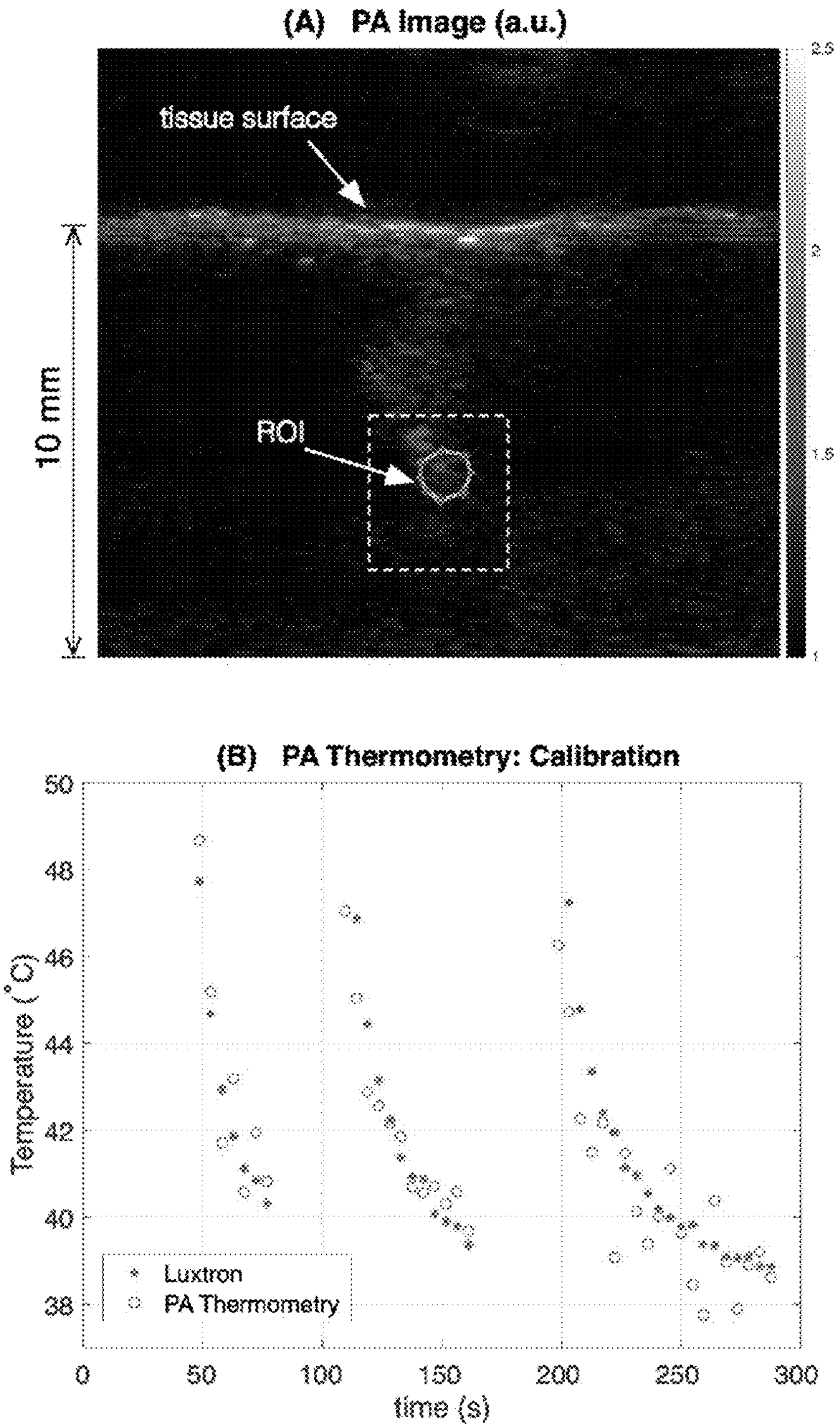

FIG. 24 illustrates a PA image of the ex-vivo tissue containing GNRs and the averaged temperature calculated from the PA images using equation (13) below. More specifically, part (A) shows a PA image of the ex-vivo tissue containing GNRs injected approximately 6 mm below the tissue surface. This image was used to locate the region of GNR accumulation in order to define an ROI using MATLAB's roipoly( ) function. Part (B) shows the averaged temperature calculated from the PA images using equation (13) below after calibration and the temperature measured using the Luxtron point-thermometry system within the ROI. This was done using three heat-cool cycles. The calibration was done by adjusting the calibration parameter in equation (13) below in order to minimize the difference between the PA-derived temperatures and the temperatures from point-thermometry.

Figure 25:
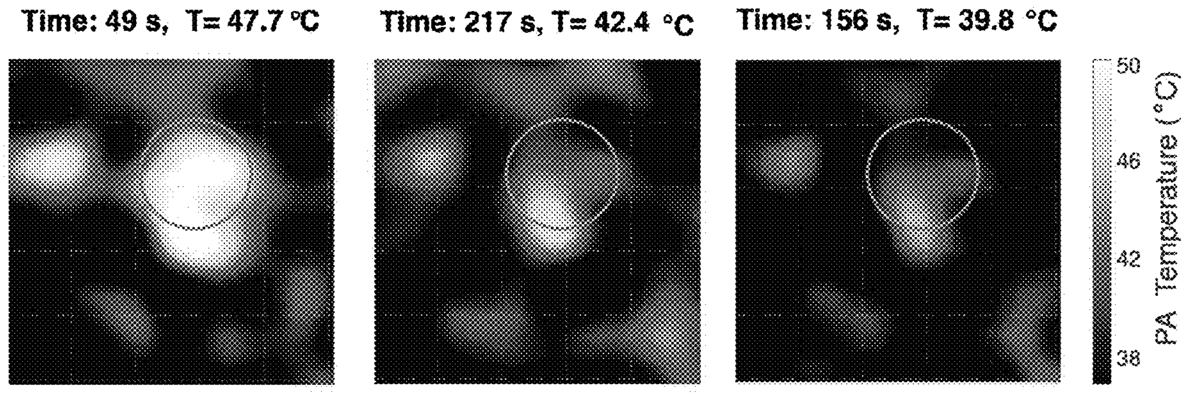

FIG. 25 illustrates PA-based temperature maps from the same experiment shown in FIG. 24. The region of the maps are bounded by the dashed yellow rectangle in FIG. 24A. The three time-points and the temperatures measured using fluoroptic point-thermometry are provided above each temperature map. The blue circles on the maps coincide with the ROI in FIG. 24A.

Figure 26:
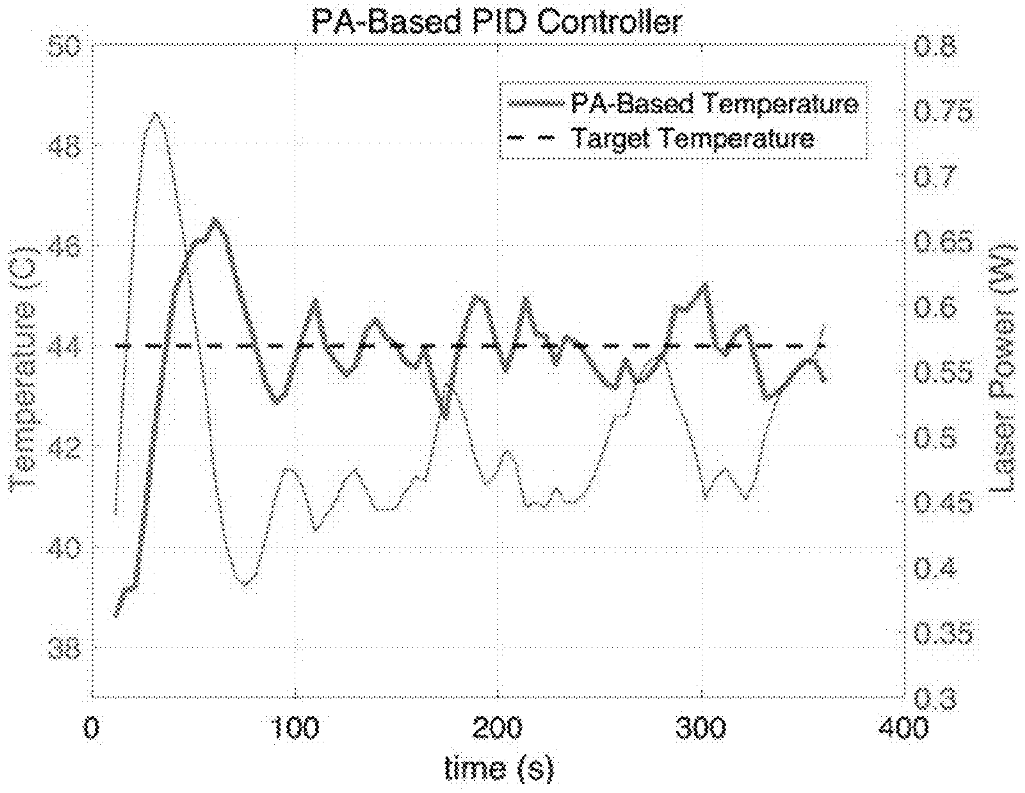

FIG. 26 illustrates experimental results of controlling laser thermal therapy based on PA thermometry. The laser power (the less bold curve and right axis) was controlled by a PID controller based on the PA thermometry (the bolder curve) to maintain a prescribed targeted temperature (the dashed line) for a six-minute treatment. The steady-state mean absolute deviation (MAD) from the targeted temperature is 0.5° C.

DETAILED DESCRIPTION OF EMBODIMENTS OF THE INVENTION

In one embodiment, an ultrasound thermometry method based on change in backscattered energy (CBE) of the acoustic harmonics is used to estimate the temperature in ex vivo tissues. Also, the feasibility of using the CBE method in detecting localized heated region generated low intensity focused ultrasound and controlling the temperature in the heated region using a temperature control system are demonstrated.

Example 1

Figure 1:
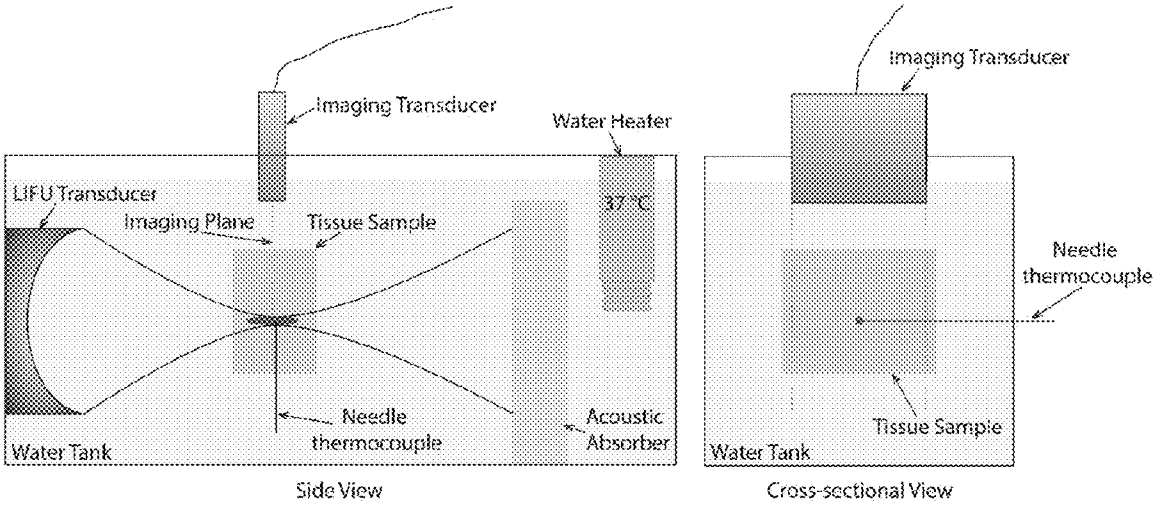
FIG. 1 is a schematic diagram of one experimental setup for an ultrasound thermometry method, according to one embodiment of the invention.
Figure 2:
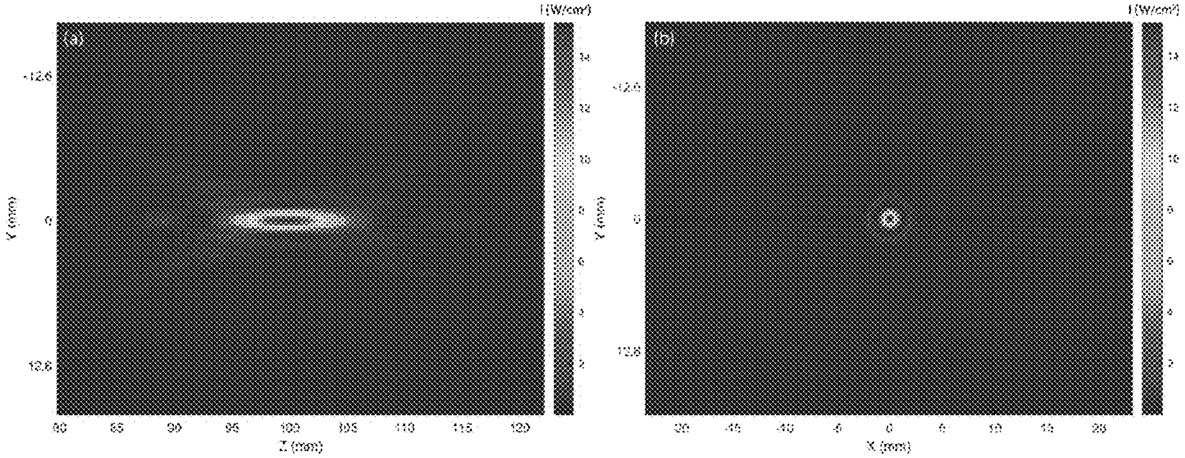
FIG. 2 illustrates a simulated intensity field of the low intensity focused ultrasound (LIFU) transducer in the (a)

Before the experiment, freshly excised ex vivo pork muscle tissue obtained from the local butcher shop was immersed in 0.9% degassed saline solution at 5° C. for 24 hours. The tissue sample was placed in a tissue holder and the dimensions of the tissue sample were 5×8×3 $cm^3$ (axial×lateral×elevational). The tissue holder was placed in a water tank housing a single-element focused therapeutic transducer (Imasonic SAS, Voray sur l'Ognon, France) that operates in a LIFU (low intensity focused ultrasound) regime. A schematic diagram of the setup is shown in FIG. 1. The therapeutic transducer had a central frequency of 1 MHz and its focal length and aperture diameter were 100 mm and 125 mm, respectively. The temperature of the water in the tank was controlled and maintained at 37° C. by a circulating water bath (Haake DC10, Thermo Electron Corp., Newington, NH). The tissue sample was exposed to 175 mVpp (corresponding to an acoustic output power of 4.5 W) burst of 1000 cycles at 1 MHz with 50% duty cycle. The baseline temperature was 37° C. and the temperature at the focal region after 6 minutes exposure time reached 47° C. The simulated intensity field of LIFU transducer generated by an acoustic field and temperature response simulator (LATS) is shown in FIG. 2. The temperature at the focal region was recorded in a separate trial by a calibrated needle type-K thermocouple and a digital thermometer (Omegaette HH306, Omega Eng. Inc., Stamford, CT). A separate imaging transducer was positioned perpendicular to the beam of the therapeutic transducer was used to acquired RF data. The imaging transducer was a linear array (L12-5 50 mm, Philips Ltd., Eindhoven, the Netherlands) connected to a research ultrasound scanner (Vantage 128, Verasonics Inc., Redmond, WA). The imaging transducer was driven by a 5 cycle burst with 4.2 MHz central frequency. The RF data was sampling with a rate of 31.25 MHz. A frame of RF data was acquired before the start of the heating as a reference and RF data frames were acquired every minute as the tissue was being exposed to LIFU beam for 6 minutes. RF data frames were acquired every minute during the LIFU exposure and for 15 minutes after turning off the LIFU.

The fundamental and second harmonic signals of the data were filtered from the acquired RF data by a bandpass filter. The backscattered energy of the fundamental ($BE_{f_0}$) and second harmonic ($BE_{h_2}$) signals were calculated by taking the envelope of the signals using Hilbert transform and then squaring the enveloped signals. In the method, the incremental change in backscattered energy $CBE_{iner}$ of each pixel (x,y) was estimated as:

$$CBE_{f_0incr}(x, y, t_n) = \frac{BE_{f_0}(x, y, t_n) - BE_{f_0}(x, y, t_{n-1})}{BE_{f_0}(x, y, t_{n-1}) + \overline{BE_{f_0}(x, y, t_n)}} \times 100, \tag{2}$$

$$CBE_{h_2incr}(x, y, t_n) = \frac{BE_{h_2}(x, y, t_n) - BE_{h_2}(x, y, t_{n-1})}{BE_{h_2}(x, y, t_{n-1}) + \overline{BE_{h_2}(x, y, t_n)}} \times 100,$$

where $t_n$ is the time at which the n-th frame of data was acquired and the bar represents the average value. The cumulative CBE maps of the fundamental and second harmonic were then computed as:

$$CBE_{f_0}(x, y, t_n) = \sum_{k=1}^{n} CBE_{f_0incr}(x, y, t_k), \tag{3}$$

$$CBE_{h_2}(x, y, t_n) = \sum_{k=1}^{n} CBE_{h_2incr}(x, y, t_k).$$

The fundamental and second harmonics CBE maps were also combined to obtain a compounded CBE map with two different frequencies (i.e., 4.2 MHz and 8.4 MHz) as follows:

$$CBE_{comb}(x, y, t_n) = \frac{\left(CBE_{f_0}(x, y, t_n) + CBE_{h_2}(x, y, t_n)\right)}{2}. \tag{4}$$

The $CBE_{h2}$ and $CBE_{comb}$ were filtered by 5×5 median and mean filters to reduce the noise in the CBE maps. Tissue motion is the main source of noise in the CBE maps. In order to reduce tissue motion between two consecutive frames, a block matching method was used. Typically, block matching methods pick a block of data from a frame and find the location where the selected block matches best with a block of data in a reference frame. In this work, a 2D normalized cross-correlation technique was used as a block matching algorithm to estimate the axial and lateral displacements between two consecutive frames using the RF data. Each frame was aligned to the previous frame based on the estimated axial and lateral displacements.

Temperature calibration was performed to determine the linkage between change in harmonic signal and change in temperature. In separate trials a calibrated needle type-K thermocouple was placed at the focus of the LIFU transducer and temperature was recorded as the tissue was being exposed to LIFU with the same parameters as the described above. This was repeated five times for different tissue samples. The linkage between percentage change in CBE and temperature was obtained from the 2D maps of CBE. A circular region with 1 mm diameter (which was determined from the simulated intensity field as shown in FIG. 2) was placed at the center of the heated region and the average percentage change in CBE was calculated for each frame. This was repeated four times for different tissue samples to reduce the inter-tissue variability. The average and standard error were calculated, and the values were tabulated as a function of temperature.

The feasibility of using the CBE methods for controlling the temperature was evaluated. A temperature control algorithm was designed to control the output of the LIFU transducer based on the estimated temperature from a calibrated needle thermocouple. The software controlled the therapeutic transducer by changing the duty cycle and applied voltage. The block of the temperature control methodology is shown in FIG. 3. The temperature control software was used to maintain the temperature at the focal region of the therapeutic transducer at 43° C. for 4 minutes. Since the presence of thermocouple was interfering with the field of view of imaging transducer, the input parameters of the therapeutic transducer to control the temperature at the focal region was determined separately from 3 trials without the imaging transducer. The average of the 3 trials was used to drive the therapeutic transducer without the thermocouple to acquire backscattered RF data with the imaging transducer to generate 2D temperature maps using the $CBE_{comb}$ method. The imaging and therapeutic transducers were synchronized so that both transducers are not on at the same time. The therapeutic transducer was turned off every 15 seconds for a duration of 250 ms to acquire a backscattered RF signal.

The temperature maps of the proposed second harmonic CBE ($CBE_{h_2}$) and combined CBE ($CBE_{comb}$) are shown in FIG. 4 and FIG. 5, respectively. The tissue sample was exposed to LIFU energy for 6 minutes and then LIFU was turned off letting the tissue to cool down for another 15 minutes. The change in temperature could be identified in all the temperature maps. In addition, the size of the heated region increased as the tissue was being exposed to LIFU energy and it decreased as the LIFU was turned off.

In order to compare with our $CBE_{h2}$ and $CBE_{comb}$ methods, temperature maps calculated from the echo-shift technique are shown in FIG. 6. The change in temperature could be identified around the focal region of the LIFU transducer. The temperature maps using the echo-shift techniques were nosier compared to the $CBE_{h2}$ and $CBE_{comb}$ techniques. This could be mainly due to the high sensitivity of the echo-shift technique to tissue motion. Even though a 2D motion compensation algorithm based on 2D cross-correlation technique was applied to the RF data to compensate for the motion in the axial and lateral directions, motion in the elevational direction and other motions and displacements were not corrected. Thus, the high sensitivity of tissue motion remains to be addressed in the echo-shift method.

The plot of the temperature measurement from the thermocouple inserted in the focal point is shown in FIG. 7. During the LIFU heating for the first 6 minutes, the temperature raised rapidly reaching an average of 46.4° C. During the cooling down period, the temperature decreased more gradually due to natural heat diffusion in the ex vivo tissue sample.

The average percentage change in $CBE_{h2}$ as a function of the average temperature reading from the thermocouple is shown in FIG. 8. The average percentage change in $CBE_{h2}$ increased with temperature. The trend between percentage change in $CBE_{h2}$ and temperature was linear. Based on the observed trend a line-of-best-fit was fitted to the data to quantify the relationship between percentage change in $CBE_{h2}$ and temperature, which was expressed as, Temperature (x,y)=0.2114×$CBE_{h_2}$(x,y)+37.18.

For the temperature control system, the $CBE_{comb}$ method was used since it was compounded of 2 different frequencies leading to noise reduction. The temperature maps of $CBE_{comb}$ is shown in FIG. 9. In this experiment, the temperature in the focal region was controlled for 4 minutes using pre-determined parameters (i.e., duty cycle and power) for the LIFU therapeutic transducer using temperature control software to maintain the temperature at the focal region at 43° C. The ex vivo tissue was let to cool down naturally while backscattered RF signal was acquired for 16 minutes. A heated spot became visible at the focal regions after 30 seconds post exposure, as shown in FIG. 9(*b*), and it diminished after 12 minutes, as shown in FIG. 9(*i*)-(*j*). The average estimated temperature from 4 trials was determined from the temperature maps and was compared with the average temperature from a calibrated needle thermocouple. The plot of the estimated temperature as a function of time is shown in FIG. 10. The temperature from the thermocouple was an average of 3 trials. The results show a rapid increase in temperature from 37° C. to 43° C. in about 1 minute, a relatively constant temperature up to 4 minutes, and a gradual decrease in temperature beyond 4 minutes. This temperature profile is chosen as a typical one that can be used in targeted drug delivery applications with e.g. thermosensitive liposomes. Temperature estimation using the $CBE_{comb}$ method shows a reasonable correlation with the thermocouple measurement. This result shows the feasibility of using the proposed $CBE_{comb}$ methods for temperature estimation and controlling. However, the main uncertainty in this result is that the temperature was not measured while the backscattered RF data was acquired. It was assumed that the temperature would be the same on the same type of tissue sample as the previous experiments where the temperature was measured by a calibrated thermocouple. The thermocouple was removed from the tissue when the backscattered RF data was acquired because it was generating artifacts in the RF echo signals acquired by the imaging transducer.

In one embodiment, the $CBE_{h_2}$ and $CBE_{comb}$ methods are used to produce 2D temperature maps. The change in temperature at the focal region of the therapeutic transducer is observed in the 2D temperature maps of the $CBE_{h2}$ and $CBE_{comb}$ methods. The increase and decrease in the size of the localized heated region was observed in the 2D temperature maps as the tissue was being heated and cooled. In the experiment, the temperature maps using the echo-shift technique appeared noisier compared to the $CBE_{h2}$ and $CBE_{comb}$ methods since the echo-shift technique is more sensitive to tissue motion.

In one embodiment, the feasibility of using the $CBE_{comb}$ method in a closed-loop feedback system was also demonstrated, where the estimated temperature from the $CBE_{comb}$ method correlated with the thermocouple measurement.

In one embodiment, an application of the $CBE_{comb}$ method is the controlled release of drugs from thermosensitive liposomes.

In one embodiment, $CBE_{comb}$ method is used with LIFU in a closed-loop feedback system to achieve a temperature of 39-43 degrees C. under software control and maintain the temperature for a desired time so as to be used to control the release of drugs from thermosensitive liposomes or antibody-coated liposomes to deliver antiproliferative agents to the cancer, such as brain tumors, skin cancer, eye cancer, mucosa cancers, genitourinary cancer, prostate cancer, lung cancer, breast cancer, mouth cancer, throat cancer, intestinal tract cancer, kidney cancer, liver cancer, urinary tract cancer, spinal cord cancer, bone cancer, spleen cancer, ovarian cancer, etc.

In one embodiment, using LIFU and controlled temperature, it is desirable to release the medication locally at a desired site and monitor and control the temperature in a range that is safe and does not induce any risk of thermal damage to tissue.

In one embodiment of thermotherapy in the treatment of a neoplasm, the rise of the temperature to about 43° C. for a period of time (e.g., 1-4 minutes) makes the tumour cells prone to damage by other adjuvant cancer treatments, such as radiation therapy, chemotherapy, gene therapy, and simultaneous immune therapy due to the fact that tumor cells, in general, have higher cell metabolism and are less efficient to cool themselves down compared to normal cells. The damage due to the controlled thermal application at about 39-43 C damages the tumor, thereby enhancing apoptosis of tumor cells and releasing tumor antigens that encourages a cellular immune response to the tumor antigens that attacks the damaged tumor cells more readily and does not give the tumor cells a chance to mount a chemical response to disguise the tumor.

In one embodiment of thermotherapy in the treatment of a neoplasm, the rise of the temperature to about 39-43° C. for a period of time causes a slight tissue expansion due to the leaky vessels during the thermotherapy leading to the collapse of the capillaries when the thermal energy is maintained beyond a few minutes that, in turn, collapses the capillaries and strangulates further the tumor cells, thereby preventing their cooling by the circulation and reduces their oxygenation and nutrition.

In one embodiment of thermotherapy in the treatment of a neoplasm, the rise of the temperature to about 39-43° C. for a period of time causes the peripheral capillaries of the tumor to become leakier and permits the medication to diffuse easier inside the tumor cells which are being damaged more precisely by the combination of thermotherapy and drug delivery using antibody-coated liposomes or nanoparticles to release the conjugated medication with the nanoparticles.

In one embodiment, the thermotherapy is combined with simultaneous imaging of the lesion before or after the treatment to observe the progression of the disease or disappearance of the tumor.

As with other non-invasive ultrasound thermometry, the method described herein requires calibration for each tissue type and transducer parameters (e.g., imaging frequency and tissue depth). The calibration becomes more challenging for heterogeneous tissues since variation between subjects is generally larger.

In one embodiment, the challenges of ultrasonic imaging may be addressed by repeating the calibration for a larger number of subjects to reduce the inter-subject variability and obtain reliable calibration information.

In one embodiment, the implementation of ultrasonic controlled thermotherapy benefits from 2D temperature maps with a high enough frame rate (at least tens of frames per minute) to control hyperthermia therapy. In order to produce a 2D temperature, the acquired backscattered data is beamformed, motion compensated and bandpass filtered (to obtain 2nd harmonic signals), then backscattered energy and change in backscattered energy is determined via the software. In some embodiments, parallel computing and/or a graphic processing unit (GPU) is used for processing the data.

In one embodiment, the method described herein with the temperature control system is used to control hyperthermia therapies.

In one embodiment of controlled thermotherapy, one can use other heating modalities, such as laser and alternative magnetic field combined with photoacoustic imaging and thermometry.

In one embodiment, for example, in veterinary applications, one can use high-frequency ultrasound scanner, such as Vevo LAZR (FUJIFILM Visualsonics, Inc., Toronto, ON, Canada) and drug-loaded thermosensitive liposomes that are activated with LIFU, laser or alternative magnetic field while the temperature is imaged and controlled by the proposed method.

In another embodiment, as described in the example provided hereinafter, an ultrasound thermometry method based on the change in backscattered energy (CBE) in a high-frequency ultrasound scanner is used to produce localized 2D temperature maps induced by an interstitial laser heating source and to control the tissue temperature non-invasively and in real-time using a closed-loop controller.

Example 2

Before the experiment, freshly excised ex vivo pork muscle tissue obtained from the local butcher shop was immersed in 0.9% degassed saline solution at 5° C. for 24 h. The tissue sample was placed in a tissue holder and the dimensions of the tissue sample were 3×4×1.5 $cm^3$ (axial×lateral×elevational). The tissue holder was placed in a temperature-controlled water bath (Haake DC10, Thermo Electron Corp., Newington, NH) to maintain the baseline temperature at 37° C. A schematic diagram of the setup is shown in FIG. 11. An interstitial laser fiber and a temperature sensing fiber were inserted into the tissue 7 mm below the surface from opposite sides with a separation distance of about 3 mm. The interstitial laser was connected to a continuous-wave diode laser heating system (BWT Beijing Ltd, Beijing, China) having an 808 nm wavelength. The laser system was connected to a personal computer (PC) workstation through a serial port interface. The temperature sensing fiber was connected to a temperature transmitter (FTX-300-LUX+, Osensa Innovations Corp., Burnaby, BC, Canada) that was connected through a USB interface to the PC workstation. A high-frequency ultrasound scanner (Vevo LAZR, FUJIFILM VisualSonics Inc.) with a central frequency of 21 MHz was used to acquire RF echo data.

The imaging plane of the transducer was perpendicular to the fibers, and it was about 1 mm away from the temperature fiber. RF echo data was exported to the PC workstation for real-time processing with a transfer rate of approximately one frame per 6 seconds. In order to reduce the tissue motion between consecutive frames, a motion compensation algorithm based on 2D normalized cross-correlation was used to compensate in the axial and lateral directions. The backscattered energy (BE) of the received RF data was calculated by taking the envelope of the signal using Hilbert transfer and squaring the enveloped signals. The incremental change in backscattered energy $CBE_{iner}$ of each pixel (x,y) was estimated as:

$$CBE_{incr}(x, y, t_n) = \frac{BE(x, y, t_n) - BE(x, y, t_{n-1})}{BE(x, y, t_{n-1}) + BE_{avg}(x, y, t_n)} \times 100, \quad (5)$$

where $t_n$ is the time at which the n-th frame of data was acquired and the $BE_{avg}$ is the average of BE data. Then the cumulative CBE maps were computed as:

$$CBE(x, y, t_n) = \sum_{i=1}^{n} CBE_{incr}(x, y, t_k). \quad (6)$$

The CBE maps were filtered by 15×15 $pixel^2$ median and mean filters to reduce the noise in the CBE maps. Then CBE maps were converted to temperature maps by using calibration data. The calibration data were obtained in separate experiments, where ex vivo tissue samples were gradually heated monotonically from 37° C. to 46° C. using the same experimental setup. The correlation between the CBE map and fiber-optic temperature measurement from the average of five different trials was estimated to be:

$$\text{Temperature}(x, y) = 0.268 \times CBE(x, y) + 36.45 \quad (7)$$

The temperature control software was a custom controller with three discrete power levels. It was designed to rapidly increase the temperature from 37° C. (baseline temperature) to 43° C. (target temperature) and to maintain the target temperature for 6 minutes. This temperature profile is able to be used in targeted drug delivery applications with thermosensitive liposomes.

The temperature map overlaid on the B-mode image at various times is shown in FIG. 12. The heated region that was about 2 mm away from the laser heating fiber is indicated by the dotted line. The average temperature in the heated region was calculated and it was used by the temperature controller to adjust the laser power. The heated region gradually became more visible, and it could be seen between 1 minute and 6 minutes when the temperature was maintained at 43° C. After 6 minutes as the laser power was turned off and the tissue sample was let to cool down naturally, the heated region gradually diminished from the temperature maps.

Some of the artifacts that appear in the temperature could be due to tissue motion. Even though the ex vivo experiment was well-controlled and tissue motion was kept minimal, tissue motion could not be completely eliminated. The main source of motion in the experiment was the circulating water in the water bath that was used to maintain the background temperature at 37° C. A 2D motion compensation algorithm was applied to the RF data to correct the translational motion in the axial and lateral directions. The average motions between each frame (measured by the motion compensation algorithm) in the axial and lateral directions were about 0.1 mm and 0.2 mm, respectively. Translational motion in the elevational direction and other more sophisticated motions were not compensated. Thus, tissue motion is one of the main issues that remain to be addressed.

The average temperature in the heated region measured from the temperature maps as a function of time is shown in FIG. 13(*a*). The temperature measurement from the fiber-optic temperature sensor is also shown for comparison. The laser power as a function of time is also shown in FIG. 13(*b*), which was adjusted based on the estimated ultrasonic temperature measurement. The temperature rapidly increased from 37° C. to 43° C. (target temperature) in about 1 minute. The temperature remained relatively constant up to 6 minutes and it gradually decreased after 6 minutes. This temperature profile is able to be used in targeted drug delivery applications, where thermosensitive liposomes loaded with therapeutic drugs can be activated at 41-43° C. The ultrasonic temperature estimation correlated well with the fiber-optic temperature measurement and the average difference between them was about ±0.8° C.

The results of this example show that the ultrasound thermometry based on CBE method generated by a high-frequency ultrasound scanner is able to be used to produce 2D temperature maps of a localized heating region in the hyperthermia temperature range (~43° C.). The estimated temperature varied by an average of ±0.8° C. compared to a calibrated fiber-optic temperature measurement. The controlled experiment showed that the target temperature could be maintained in a localized region of interest in ex vivo tissue for as long as it is required.

In one embodiment, a robust real-time non-invasive ultrasound thermometry method is used to enhance the effectiveness and safety of the thermal therapy either as a direct treatment modality or as an adjuvant to other therapeutic modalities, such as chemotherapy and radiation therapy. Moreover, in one or more embodiments, it can be used in targeted drug delivery systems such as heat-activated drug release using thermosensitive liposomes.

In one embodiment, the system described in the above example is used to control a heated tissue temperature in real-time during thermal therapy.

In one embodiment, a non-invasive ultrasound thermometry method based on the CBE technique is used for real-time monitoring and control of hyperthermia treatments, using interstitial laser heating source with acceptable accuracy.

Example 3

The mechanisms of drug release from thermosensitive liposomes depend on the thermal and mechanical effects of ultrasound. As described hereinafter, an in vitro setup with custom 3D-printed sample holders embedded in tissue was used to evaluate the drug release from thermosensitive liposomes upon ultrasound exposure with exposure parameters that would induce either thermal and/or mechanical effects. In the thermal heating exposure experiments, the output of the 1 MHz transducer was controlled with a feedback controller based on temperature control. The temperature was measured using a calibrated needle thermocouple to maintain a 43° C. temperature for 5 minutes, which resulted in a fractional release of 0.96±0.27. Water-bath thermal heating at 43° C. temperature for 5 minutes was also performed for comparison, resulting in a similar fractional release (0.88±0.26). For the mechanical non-thermal ultrasound exposure parameters, a 1 MHz transducer was used to generate 25 ms pulses at a pulse repetition frequency of 1 Hz and with a focal peak pressure of 3.3 MPa for 30 seconds. The exposure to mechanical parameters also resulted in significant fractional release of 0.76±0.37. The exemplary experiment described hereinafter demonstrates how 3D-printed sample holders can be used to measure ultrasound-mediated drug release, and how both thermal and non-thermal methods could be used to achieve the release.

Prior to conducting the experiment, 1,2-dipalmitoyl-sn-glycero-3-phosphatidylcholine (DPPC) was obtained from Avanti Polar Lipids, Inc. (Alabaster, AL, USA). Brij® S2, HEPES were purchased from Sigma-Aldrich (St Louis, MO, USA). Isopropanol was obtained by Caledon Laboratories Ltd (Halton Hills, ON, Canada). Doxorubicin hydrochloride was purchased from LC Laboratories (Woburn, MA, USA) and was dissolved in DMSO at 100 mg/ml stock solution concentrations, and the aliquots were kept at −20° C. The aliquots were then de-frosted and were diluted in Milli-Q water at 1 mg/ml working solutions that were kept at 4° C., which was further diluted at appropriate dilutions prior to use. RPMI1640, Phosphate Buffered Saline (PBS), Fetal bovine serum (FBS), Penicillin-streptomycin, Trypsin/EDTA 0.25% were obtained by Wisent Inc. (St-Bruno, QC, Canada).

Preparation of the thermosensitive liposome formulation with encapsulated doxorubicin was modified with liposomal lipid, DPPC, and a non-ionic surfactant consisting of PEGylated acyl chains, Brij® S2, at a composition of 96:4 mol %. The liposomes were formed using the thin film hydration method. Briefly, 100 mg of lipids were dissolved in 10 mL of isopropanol. The solution was aliquoted to 1 mL batches in glass vials, and the solution was dried by a stream of nitrogen gas, followed by overnight desiccation under vacuum. The lipid film was hydrated with doxorubicin at a 0.05 drug:lipid ratio at a temperature above the main phase transition temperature of 41.3° C. for complete lipid swelling and hydration. The lipid solution was extruded 9 times through a polycarbonate disk, and two stacked 0.1 μm filter supports at a temperature above the main phase transition temperature. Non-encapsulated doxorubicin was removed using dialysis against the HEPES loading buffer. The particle size and concentration were determined by resonant mass measurement using Archimedes (Malvern Panalytical Ltd., Malvern, UK). Doxorubicin fluorescence assay was used for the quantification of loaded doxorubicin. Briefly, Triton X-100 was added to the liposomal doxorubicin to produce a 1% v/v final concentration of the detergent. Then the fluorescence (Ex 485 nm/Em 590 nm) was measured with a multimode plate reader (Molecular Devices, San Jose, USA) and compared to a doxorubicin standard curve. The loaded liposomes were either used immediately or stored at room temperature and then used within 48 h.

Doxorubicin release was determined using a fluorescence de-quenching assay. The fractional release of doxorubicin was calculated as:

$$R = \frac{I_x - I_0}{I_{100} - I_0}. \tag{8}$$

where R is the fractional release, $I_x$ is the fluorescence of the treated sample, $I_0$ is the fluorescence of a non-treated sample, and $I_{100}$ is the fluorescence of the sample treated with 1% Triton X-100 (vol/vol). Triton X-100 is a detergent that lyses the liposomes and therefore corresponds to the completely released drug fluorescence reference. The fluorescence (Ex 485 nm/Em 590 nm) was measured with a multimode plate reader (Molecular Devices, San Jose, USA).

Freshly excised ex vivo porcine muscle tissue was obtained from the local butcher shop and was immersed in a 0.9% de-gassed saline solution at 4° C. for 24 hours. Then, the tissue was pre-heated to 37° C. by immersing the tissue-containing beaker in a water bath. The heated tissue was placed in a 3D printed tissue holder with the dimensions of 3×8×5 $cm^3$ (axial×lateral×elevational) which is designed to be suspended on the upper axial edges of the water tank. The surface parallel to the transducer was previously enclosed with a transparent cellophane film with a thickness of approximately 40 μm, which reduces the acoustic impedance compared to using relatively thicker polystyrene tubes. The doxorubicin-loaded liposomes were placed in a 3D printed sample holder, with a loading dimension of 0.5×1×1 $cm^3$ (axial×lateral×elevational), where the surface that will be placed parallel to the transducer was previously enclosed with transparent cellophane film. On the lateral side of the sample holder, a port was designed for sample loading/unloading, and miniature screws were used enclose the port. The sample containing holder was then inserted in between the ex vivo porcine muscle tissue containing holder. A diagram of the sample and tissue holders are shown in FIG. 14D. With these holder designs, the liposomal samples were able to be embedded within the ex vivo tissue without injection directly into the tissue, therefore, the sample was able to be retrieved after the ultrasound treatments for sample analysis.

The samples were exposed to focused ultrasound in two different exposure regimes: (a) low intensity focused ultrasound (LIFU) for thermal, and (b) pulsed high intensity focused ultrasound (pHIFU) for mechanical exposures. A 1 MHz single-element therapeutic transducer was used (IMASONIC SAS, Voray sur l'Ognon, France) with a focal length and diameter of 10 cm and 1.25 cm, respectively. The temperature of the water in the tank was controlled and maintained at 37° C. by a circulating water bath (Haake DC10, Thermo Electron Corp., Newington, NH). Calibrated needle type-K thermocouples and a digital thermometer (Omegaette HH360, Omega Eng. Inc., Stamford, CT) were also placed in the sample holder and in the ex vivo tissue sample close to the LIFU focal zone for temperature measuring, monitoring and control purposes. The setup is shown in FIGS. 14A-14C, and the ultrasound parameters used for the experiment are shown in FIG. 15, which contains Table 1. The output acoustic power was measured by radiation force balance (RFB-2000, ONDA Corp., Sunnyvale, CA) and the focal peak pressures were measured with a needle hydrophone (HNA, ONDA Corp., Sunnyvale, CA) that was placed at the focus of the LIFU transducer.

Compared to continuous HIFU, pulsed HIFU (pHIFU) with low duty cycles (<10%) can significantly reduce the temperature rise and may be used to promote the mechanical effects such as acoustic cavitation. To limit unspecific heat damage to normal tissues, low-intensity focused ultrasound (LIFU) can be used in combination with drug carriers (such as thermosensitive liposomes). In this approach, the payloads are delivered at a few degrees above physiological temperatures. Thermosensitive liposomes are drug delivery systems that release the encapsulated drug when heated to hyperthermia temperatures at 41-43° C. At these temperatures, it has also been shown that nanoparticle extravasation increases, likely due to increased pore sizes between endothelial cells and increased intravascular blood flow. The mechanism for mechanical release in the absence of a temperature increase is not well known. Mechanical release can be caused from high mechanical stresses on the drug carrier shell using short ultrasound pulses causing membrane rupture and generation of membrane pores. In this experiment, doxorubicin was released in response to LIFU (thermal) and pHIFU (mechanical) exposure in a custom 3D-printed sample holder that is embedded in tissue.

The final size of the liposomes was 212±19 nm with a polydispersity index (PDI) of 0.25±0.1 (n=8 independently synthesized batches) measured with Archimedes (Malvern Panalytical, Malvern, UK) a particle metrology system using a resonant mass measurement method. The drug to lipid ratio after removing the non-encapsulated doxorubicin was 0.01, achieving approximately 20% of doxorubicin passive loading. This loading is within the expected range of passive encapsulation efficiency of water-soluble drugs in liposomes. The liposomes were freshly prepared for each of the experiments.

The liposome sample was inserted in the tissue that was pre-heated to 37° C. The output of the LIFU transducer was controlled based on the temperature measured from a calibrated needle thermocouple. The software controlled the transducer by changing the duty cycle and applied voltage. Once the liposome sample also reached 37° C., the designed temperature control software was used to maintain the temperature of the liposome samples at a pre-determined temperature (43° C.) and time period (5 min). The temperature was measured for another 5 minutes after the LIFU was turned off to record the cool-down trend. A representative temperature profile measured with the calibrated thermocouple placed inside the liposome sample holder is shown in FIG. 16.

The release of doxorubicin from the liposomes upon exposure to the water bath, LIFU, and pHIFU is shown in FIG. 17. A fluorescence de-quenching assay has been used to measure the release. The parameters for LIFU and pHIFU are shown in FIG. 15, which contains Table 1. The increase in bulk temperature up to 43° C. for 5 min resulted in the complete release of doxorubicin, regardless of the heating source (water bath or US, fractional release of 0.88±0.26 and 0.96±0.27 (n=5) respectively). These results indicate that the thermosensitive liposomes disintegrate and release the loaded drug when the bulk temperature is increased above the threshold temperature. The thermosensitive liposomes used to encapsulate the doxorubicin has lipid bilayer has a phase transition temperature (Tc) within the range of tolerable local-regional hyperthermia at approximately 42-43° C., above normal body temperature of 37° C. The lipid molecules below the Tc are condensed with fully extended hydrocarbon chains and constrained to form an impermeable membrane. In response to heating, the mobility of the lipid head group increases and as the temperature reaches the Tc, the orientation of the C—C single bonds in the hydrocarbon chains switch from a trans to a gauche configuration, disorganizing the lipid molecule packing and enhancing permeability. At temperatures above Tc, the lipid bilayer exists fully in the liquid phase, and the membrane is permeable throughout, releasing the loaded contents.

Significant drug release of 0.76±0.37 (n=3) was also observed from specific non-thermal ultrasound exposures where the bulk temperature increase was less than 0.5° C. These results indicate that the combined drug-loaded liposome therapy with ultrasound exposures can lead to enhanced efficacy even without bulk temperature increase. The mechanism for mechanical release is not well understood. It has been hypothesized that the mechanical release of drugs can be caused by high mechanical stresses on the drug carriers using short ultrasound pulses. The short, intense pulses could cause membrane rupture and generation of membrane pores induced by acoustic cavitation, the formation of gas or vapour filled cavities in a medium exposed to high oscillating pressure. Although bubbles were not initially injected, gas bodies dispersed in the sample may serve as cavitation nuclei and form natural microbubbles under the high-intensity ultrasound waves. The formed bubbles can collapse within the focal point of the ultrasound and disrupt the lipid bilayer and produce temporary pores in the liposome membrane. The transient permeabilization of the lipid bilayer is referred to as sonoporation, and from these temporary pores, the contents of the liposomes can be released.

The unique setup allowed the quantification of drug release in freshly excised ex vivo porcine muscle tissue that was exposed to ultrasound. The ultrasound exposures created bulk tissue heating or induced non-thermal drug release due to the mechanical perturbation of the liposomal formulation. Several aspects of the 3D-printed holder have been modified since the initial design and form the basis for future work. For example, initially the holder was rectangular with a loading window but it evolved to become the current T-shaped with a narrowing bottom edge to place the sample holder more accurately within the focal region. Holders with different dimensions and/or designs may be required to use with different transducers. The use of a 3D printer allows the customization of the holder to the target dimensions.

A unique setup with 3D printed sample holders enclosed with cellophane film was designed to measure the release of doxorubicin from thermosensitive liposomes in response to both thermal and mechanical (non-thermal) parameters of ultrasound with a 1 MHz transducer. A complete release of the drug was observed when the bulk temperature was increased to 43° C. by both water bath heating and LIFU exposure, indicating that at 43° C., the lipid bilayer exists in the liquid phase and the membrane is permeable throughout. Significant drug release was also induced by using exposure parameters that led to non-thermal drug release. These results indicate that the mechanical stresses from the ultrasound pulses may have ruptured the liposomal membrane causing the release of the drug content.

In one embodiment, significant drug release was induced by exposing the drug-loaded thermosensitive liposomes with both thermal and non-thermal mechanical parameters of ultrasound with a 1 MHz transducer.

In one embodiment, one can implement the non-invasive temperature measurements and control for the hyperthermal treatments in which the methodologies are currently in development for drug release for any medication used in any part of the body, for drug delivery in any drug, such as bacterial, viral, fungal, or parasitic infection, or for delivery or antibodies, or medications at a precise location of the internal of external part of the body.

In one embodiment, the nanoparticles can be of any size 1 nm to micron size, ball, cylindrical rod shape hollow, of filled metallic, non-metallic, organic, synthetic, magnetic, paramagnetic, coated with antibodies for specific cell or tumor, etc. or micelles, liposomes, etc. filled up with other nanoparticles or medications or genes, hormones, poison, venom, immune stimulators or cell pathway inhibitors, anti-inflammatory or vaccines needed to be delivered at a specific body part to stimulate humoral or cellular immune response locally or systemically.

In one embodiment other heating modalities, including laser and alternating magnetic field (AMF), microwave, radiofrequency, or any electromagnetic radiation can be used as sources of external stimuli.

In one embodiment, the biological effect of the combined drug-filled thermosensitive liposome and external stimuli will be observed through imaging, sensor or electrophysiology or liquid biopsy, chemical or non-invasive optical or non-optical imaging, etc. means.

In one embodiment, low-intensity focused ultrasound has a focal intensity of a few tens of W/cm$^2$ and results in the temperature rise of 41-45° C. To limit unspecific heating damage, LIFU can be used in combination with drug carriers that deliver the payloads at a few degrees above physiological temperatures, such as thermosensitive liposomes. Thermosensitive liposomes are drug delivery systems that release the encapsulated drug when heated to hyperthermal temperatures at 41-43° C.

In one embodiment, at low hyperthermal temperatures, during the controlled thermotherapy, the nanoparticle extravasation increases due to increased pore sizes between endothelial cells and increased intravascular blood flow.

In one embodiment, the focused ultrasound is used as a short pulse of milliseconds with high power to cause mechanical damage to the wall of the liposomes producing breakdown/pores in the liposome's wall or the nanoparticle polymeric coating, carrying the medication, thereby releasing the medication, or liposome membrane rupture with generation of membrane pores being induced by acoustic cavitation, and the formation of gas or vapor-filled cavities in a medium exposed to oscillating pressure.

Example 4

A proportional-integral-derivative (PID) controller (FIG. 18) was developed with the goal of getting the measured temperature, T (t), to track the prescribed reference temperature, $T_r(t)$, as closely as possible. The three-term functionality enables treatment for both steady-state and transient response and makes PID offer the simplest, but also the most efficient solution to real-world control problems. The tracking error, $e(t)=T_r(t)$ T (t), along with the time integral and the time derivative of this error were used to calculate the current, I(t), that drives the lase. $K_p$, $K_i$, and $K_d$ are the proportional, integral, and derivative coefficients, respectively. These values were tuned to optimize the tracking. This was done by first conducting a series of experiments using the Ziegler-Nichols method to get initial values for these coefficients. Then on-site manual PID tuning was performed that is widely used to further improve the efficiency and accuracy of the controller.

The Vevo LAZR system was used with a 21 MHz ultrasound transducer and a nanosecond excitation laser that could operate in the wavelength range of 680 nm-930 nm. The system produces high-resolution PA and ultrasound images and is widely used in small animal experiments. The data is usually saved on the system during imaging and later exported for post-processing and analysis using the VevoLAB software. Co-registered PA and ultrasound frames were exported in real-time to the computer running the control system. The transfer rate was approximately one frame per three seconds. MATLAB code was written to be run on the controlling computer in order to read the PA images in real-time for the feedback controller. The PA (and ultrasound) images are used by an operator to identify the region-of-interest for which the temperature needs to be monitored prior to the treatment.

A high-power continuous-wave (808 nm, up to 15 W) diode laser system (BWT Beijing Ltd, Beijing, China) was used as the heating laser. This laser system could be accessed either through its front control panel or through a serial port connected to a computer. MATLAB code was created that activated and turned on and off the laser system, and controlled the driving current or the output power of the laser in real-time through its serial port interface.

Point thermometry was used to verify and calibrate the PA-based thermometry and to conduct primary PID controller testing, validation, and tuning. A fluoroptic thermometry system (3100 Series Fluoroptic Thermometer, Luxtron Corporation, Santa Clara, CA) was used for this purpose in order to avoid artifacts caused by the interaction of the laser with traditional metal thermocouples. The fluoroptic thermometry system was also interfaced to the controlling computer through a serial port connection. MATLAB code was used to activate the system, acquire temperature measurements in real-time, and deactivate the system.

The ability of photoacoustic imaging to provide both structural and functional imaging at the same time has led to investigations of its use in diverse application areas, such as temperature monitoring of tissue. Understanding how this is done requires a mathematical model of photoacoustic imaging.

The initial pressure generated at location x in tissue due to the photoacoustic effect is given by:

$$p0(x)=\Gamma(x)\mu_a(x)\varphi(x), \tag{9}$$

where $\mu_a(x)$ is the absorption coefficient, $\varphi(x)$ is the light fluence (note that $\mu_a\varphi(x)$ is the absorbed optical power density), and $\Gamma(x)$ is the Gruneisen parameter. The Gruneisen parameter relates the initial pressure increase to the absorbed power density and is given by:

$$\Gamma(x)=\frac{\beta(x)c(x)2}{Cp(x)} \tag{10}$$

where $\beta(x)$ is the thermal coefficient of expansion, c(x) is the velocity of sound, and $C_p(x)$ is the specific heat capacity at constant pressure. Since the Gruneisen parameter has been found to be temperature dependent the initial PA signal is also temperature dependent. The Gruneisen parameter's dependence on temperature can be described by an affine function:

$$\Gamma(x,T)=a0(x)+a1(x)T(x). \tag{11}$$

We assume that the PA image intensity at location x is proportional to the initial pressure at that location: I(x) p0(x). We also assume in the hyperthermic temperature range only the Grüneisen parameter varies with temperature while the optical absorption coefficient does not. The ratio of the PA image intensity at some temperature, I(x, T), to the image intensity at the baseline temperature, $I_b(x, T_b)$ is given by:

$$RR(x,T)=\frac{I(x,T)}{I(x,T_b)}=\frac{p(x,T)}{p(x,T_b)}=\frac{\Gamma(x,T)}{\Gamma(x,T_b)}=\frac{a0(x)+a1(x)T}{a0(x)+a1(x)T_b} \tag{12}$$

Hence, the temperature value based on PA thermometry is given by:

$$T(x) = [a(x) + T_b(x)]R(x, T) - a(x), \quad (13)$$

where a(x)=a0(x)/a1(x) is the only parameter that needs to be determined when calibrating the PA thermometry system for a certain medium or tissue type.

In the experiment, gold nanorods (AuNR) are prepared by a modified version of the seeded growth method.

Seed preparation: The synthesis is performed in a water bath at 30° C. After adding 50 μL of 1% HAuCl4 solution to 4.7 mL of 0.1 M of CTAB, the mixture is slowly stirred for 5 min until no signs of turbidity. Then 300 L of freshly prepared 10 mM of NaBH4 under rapid stirring. The solution is then stirred mildly before use.

Growth: A solution of 200 μL, 1% HAuCl4 is added to 10 mL of 0.1 M stirred gently for 10 min to ensure complexation between the gold salts and CTAB. Then, 75 μL of 0.1 M ascorbic acid is added to the mixture so that the solution turns colourless. A solution of 80 μL of 5 mM AgNO3 is added to the growth solution. Finally, 120 μL of seeds solution is added to the mixture and the solution is stirred vigorously and then left undisturbed in the water bath.

The CTAB stabilized AuNRs filtered twice and were purified by centrifugation (10,000×g for 50 min) and re-dispersed in ultrapure water (MilliQ), followed by second centrifugation at 7,000×g for 30 min. The concentration of the GNR is estimated to be 0.286 mg/ml measured with the ICP-AES.

Two types of experiments were performed. One involved heating the surface of tissue using an end-cut fibre radiating onto the tissue surface and the other involved heating deep in tissue using an interstitial heating fibre. These two types of experiments were conducted to study the performance of the control system until varying conditions.

(1) Surface heating: The surface laser heating experimental setup is shown in FIG. 19. The tissue was exposed to air and was equilibriated to room temperature before heating. This setup was used to investigate the ability to achieve the desired temperature rise, as well as the ability to measure and control the temperature using the Luxtron fluoroptic thermometry system for surface heating. As shown in FIG. 19, the heating laser fibre was placed 3 to 5 mm above a pork loin tissue. The tip of the Luxtron fluoroptic fibre was inserted just below the tissue surface in the middle of the irradiating field from the heating laser. In the same location, GNRs were injected just below the tissue surface. This caused the GNRs to settle both on top of the tissue surface and just below the surface. This setup was also used to investigate the laser heating enhancement achieved by using different concentrations of GNRs (0.286 mg/ml, 0.143 mg/ml, and 0.0286 mg/ml).

(2) Deep-tissue heating: The experimental setup used for PA thermometry calibration and thermal therapy control is shown in FIG. 20. Pork loin was placed in a holder and kept in a 37° C. hot water-bath after injecting 50 μL of GNR solution (0.286 mg/ml) 5 mm below the surface. A fluoroptic thermometry fibre was inserted into the location where GNRs were deposited in the tissue, while a heating laser fibre was inserted between 2.5 mm and 5 mm away from the thermometry fibre. These insertions were done with using guiding holes in the holder. Photoacoustic images of the tissue were streamed into a controlling computer, which acquired simultaneous temperature measurements using the fluoroptic thermometer (Luxtron). The change in the PA signal due to heating was fitted against the actual temperature measurements to produce an initial PA thermometry calibration parameter (from equation (13)). Consequently, the fluoroptic thermometry fibre (gray colour in FIG. 20) was removed, and non-invasive PA thermometry was used as the lone feedback to control the laser power in order to keep the tissue at a prescribed targeted temperature. This was achieved by the PID controller that ran on the controlling computer.

Results for the effect of GNRs on laser heating is presented first followed by control of laser heating with GNRs using the Luxtron point-thermometry system. This is followed by results from the PA thermometry that was developed and finally by results of the control of GNR based laser thermal therapy using PA thermometry.

The enhancement in tissue laser heating by GNRs at various concentrations was investigated. Using the surface laser heating setup (FIG. 19), the sample was first heated for 200 seconds with no GNRs. Subsequently, the same tissue was injected with 50 μL of in-house synthesized GNRs (0.286 mg/ml), just below the tissue surface. While the same laser power was used, the GNR substantially enhanced the heating as shown by the three upper curves in FIG. 21. Then, the heating with different GNR concentrations was repeated, injected just below the tissue surface. The results are shown in FIG. 21 shows that even with 10% of the original GNR concentration a significant heating enhancement can be achieved.

The control of heating at the surface and below the surface of pork loin tissue was investigated.

(1) Surface laser-heating control: The results were obtained using the setup shown in FIG. 19, with the heating laser fibre placed 5 mm above the pork loin tissue. FIG. 22 shows that the prescribed temperature rise for hyperthermia applications was able to be achieved, of around 7° C., by surface irradiation; the heating temperature was also able to be measured and controlled using a PID controller. The PID parameters from the deep-tissue heating experiment described in the next section were used. Hence, even more accurate control should be achievable by further tuning the PID parameters for this surface irradiation case.

(2) Deep-tissue laser-heating control: The ability to control laser heating deep in tissue using interstitial fibre light delivery and changing the desired temperature, $T_r(t)$, in various stages is demonstrated in FIG. 23. The prescribed treatment was $T_r(0<t<150\text{ s})=41°$ C.; $T_r(150\text{ s}\leq t<270\text{ s}=44°)$ C; and $T_r(270\text{ s}\leq t<420\text{ s}=41°$ C. The PID controller developed was used to control the laser thermal therapy based on the temperature measured using fluoroptic thermometry. By tuning the PID coefficients, the following values were obtained: $K_p=1.2$ AK$^{-}$1, $K_i=0.15$ AK$^{-}$s−1, and $K_d=0.01$ AK$^{-}$1s.

PA imaging and PA thermometry of deep heating was tested using the experimental setup shown in FIG. 20. The heating laser was turned on and off three times during a 5 minute time period. FIG. 24A shows a PA image frame that was initially acquired to select the region of interest (ROI) before starting the heating process. The spatially averaged PA image intensity in a region of interest (ROI) was determined for each PA frame. A fitting was performed between the temperature measured using the Luxtron point thermometry system and the temperature calculated from the PA imaging using equation (13). This resulted in a calibration parameter value of a=115° C. The result of the fitting/calibration is shown in FIG. 24B.

FIG. 25 shows the PA temperature maps derived after this calibration, in the region bounded by the dashed yellow rectangle in FIG. 24A. The points were chosen to reflect different levels of temperature during the heating-cooling process (high, mid, and low).

The same setup (FIG. 20) that used for the results described in the PA thermometry testing described above was used to control the spatially averaged temperature in the ROI similar to the one shown in FIG. 24A. The control was based solely on real-time PA thermometry, without any invasive point thermometry. The heating laser fibre was about 3 mm away from a region of interest (ROI) where GNRs are located. The laser power was controlled using a PID controller with the tuning parameters, $K_p$=25 mWK$^{-}$1, $K_i$=5 mWK$^{-}$1s−1, and $K_d$=0.5 mWK$^{-}$1s. The performance of the controller is shown in FIG. 26. The controller was able to maintain the temperature in the ROI at 44° C.±1.5° C. within approximately 1 min. after turning on the heating laser. There was a noticeable overshoot of approximately 2.5° C. before control was reached.

The above-described experiments investigated real-time control of GNR mediated laser thermal therapy using PA imaging. Specifically, ex-vivo experiments were performed to establish the feasibility of using the VisualSonics Vevo LAZR system for the monitoring and control of temperature rise in hyperthermia treatments. While the experiments focused on GNR mediated laser thermal therapy, they introduced a simple, practical framework to build a non-invasive controller for a wide range of thermal therapy modalities using the Vevo LAZR system. This system is widely used for small animal pre-clinical research. The system produces high-resolution photoacoustic and ultrasound images which, when combined, produce a variety of anatomical, functional and molecular information. These capabilities, along with other features like compensation for respiratory motion, make the Vevo LAZR system a versatile tool for the monitoring and control of many types of treatments that are based on heating.

The use of GNRs both enhances the laser heating process and improves the SNR of the PA signal. Both of these enhancements are only possible if the photoacoustic pulsed laser and the heating continuous-wave (CW) laser operating near the absorption peak of the GNRs (808 nm in this work). This two-fold benefit motivates the inclusion of GNRs in targeted drug delivery using thermosensitive liposomes. The embedding GNRs into the liposomes will facilitate both imaging of the liposome accumulation using PA imaging and the release of the drug, using a CW laser directed at the target region.

The above-described experiments demonstrate the use of PA thermometry, obtained from a commercially available imaging system, in controlling thermal therapy. The results obtained also confirm that the magnitude of the PA signal increases when the temperature rises and that a single calibration parameter could be used to obtain an absolute temperature from the relative changed in the PA intensity.

As described above, a PID controller for laser thermal therapy using based on invasive point temperature measurement was developed and tested, and it was demonstrated that this approach could achieve the prescribed temperature profile for both surface heating and deep-tissue heating. Subsequently, these results were used to perform non-invasive temperature control experiments, where the heating power was controlled by a PID controller using PA thermometry. The performance of the PA-based PID controller (in FIG. 26) can be improved by further tuning its parameters. Further improvement to the controller could be achieved by embedding the control system into the Vevo LAZR system. This would avoid exporting the images to the hard-disk of the computer running the control system, resulting in a substantially higher rate at which PA frames are obtained (which is around 3.5 seconds for the current setup).

In one embodiment, PA thermometry obtained from a photoacoustic imaging system was used for feedback in PID control of GNR mediated laser thermal therapy. The first completely non-invasive real-time controller for hyperthermia based on PA thermometry was utilized. This was done using the VisualSonics Vevo LAZR system that produces high-resolution PA and ultrasound images. The system is easy to use and comes with a wide range of modalities and real-time features. Introducing thermal therapy monitoring and control based on such a system can lead to the widespread use of the non-invasive PA thermometry in effectively controlling thermal therapies. The monitoring and control methods can also be used in other thermal therapy related treatments and applications.

In one embodiment, an automated control system for hyperthermia therapy that can accurately achieve a prescribed temperature for both surface heating and deep-tissue heating was developed and tested. A non-invasive PA thermometry using a high-frequency PA imaging platform (e.g., the Vevo LAZR system from FUJIFILM Visualsonics, Inc., Toronto, ON, Canada) was implemented. The Vevo LAZR system is useful for oxymetry, nanoparticle-mediated imaging and therapies, vascular imaging, and nanoparticle drug delivery systems. Advantageously, the ability to perform PA thermometry in real-time using the Vevo LAZR system in order to control heating (using any modality) enables a broad range of new possibilities in the pre-clinical setting, such as targeted thermal therapy, drug delivery using thermosensitive liposomes, thermal radiosensitization and thermal enhancement of chemotherapy.

In one embodiment, the PA imaging system was interfaced to obtain PA images while scanning ex-vivo tissue. These images were then used to obtain temperature maps in real-time during heating. Validation and calibration of the PA thermometry were done using a flouroptic thermometer. This thermometer was also used to develop and tune a software-based proportional integral derivative (PID) controller. Finally, a PA-based PID closed-loop controller was used to control gold nanorod (GNR) mediated laser thermotherapy for the desired temperature and time period.

In one embodiment, the use of GNRs substantially enhanced laser heating; the temperature rise increased to 7-fold by injecting a GNR solution with a concentration of 0.0286 mg/mL. The control experiments demonstrated that the desired temperature could be achieved and maintained at a targeted location in the ex-vivo tissue. The steady-state mean absolute deviations (MAD) from the targeted temperature during control were between 0.16° C. and 0.5° C., depending on the experiment.

In one embodiment, hyperthermia treatments were controlled using a software-based PID controller and a PA imaging system. The monitoring and control of the temperature in thermal-based therapies are important for assuring a prescribed temperature to the target tissue while minimizing the temperature of the surrounding healthy tissue. Advantageously, the easily implemented non-invasive control system described above facilitates the realization of a broad range of hyperthermia treatments.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A cancer treatment method using nanoparticle-mediated thermal therapy and photoacoustic imaging, the method comprising the steps of:

administering a plurality of nanoparticles to tissue at a site of a tumor in a patient, the plurality of nanoparticles administered to the tissue at the site of the tumor in the patient comprising gold nanoparticles embedded in liposomes, the liposomes containing an anti-tumor medication;

heating the tissue and at least some of the plurality of nanoparticles at the site of the tumor in a plurality of different heating stages using a thermal energy source so as to generate photoacoustic signals, damage one or more tumor cell membranes, and release antigenic material in vivo that activates and stimulates an immunogenic response of the patient at the site of the tumor, the thermal energy source operating near an absorption peak of the gold nanoparticles;

performing photoacoustic imaging with a photoacoustic imaging unit so as to acquire the photoacoustic signals; and determining, by using the photoacoustic imaging unit, a temperature of the heated tissue at the site of the tumor from the photoacoustic signals;

wherein the step of heating the tissue and the at least some of the plurality of nanoparticles further comprises heating at least some of the gold nanoparticles at the site of the tumor, the heating of the gold nanoparticles resulting in an increased temperature rise at the site of the tumor that is five to seven times greater than a temperature rise achieved without the administration of gold nanoparticles;

wherein the embedded gold nanoparticles in the liposomes facilitates the photoacoustic imaging of accumulated ones of the liposomes at the site of the tumor, and facilitates release of the anti-tumor medication at the site of the tumor;

wherein the plurality of different heating stages comprise a first heating stage at a first predetermined temperature for a first duration of time, a second heating stage at a second predetermined temperature for a second duration of time, and a third heating stage at a third predetermined temperature for a third duration of time; and wherein the second predetermined temperature is greater than the first and third predetermined temperatures, and the second duration of time is less than the first and third durations of time.

2. The cancer treatment method according to claim 1, further comprising a proportional-integral-derivative (PID) controller operatively coupled to the thermal energy source and the photoacoustic imaging unit; and wherein the step of heating the tissue and the at least some of the plurality of nanoparticles at the site of the tumor further comprises controlling the thermal energy source using the proportional-integral-derivative (PID) controller based on the temperature determined by the photoacoustic imaging unit in order to heat the tissue and the at least some of the plurality of nanoparticles to a prescribed temperature so as to provide real-time control of nanoparticle-mediated thermal therapy.

3. The cancer treatment method according to claim 1, wherein the thermal energy source for heating the tissue is selected from the group consisting of laser, ultrasound, an alternating magnetic field, microwave radiation, and radiofrequency (RF) energy.

4. The cancer treatment method according to claim 1, wherein the photoacoustic imaging unit comprises an ultrasound transducer and a nanosecond excitation laser.

5. The cancer treatment method according to claim 4, wherein the ultrasound transducer of the photoacoustic imaging unit operates at a frequency of 21 megaHertz and the nanosecond excitation laser operates in a wavelength range of 680 nanometers to 930 nanometers.

6. The cancer treatment method according to claim 1, wherein the anti-tumor medication comprises doxorubicin.

7. The cancer treatment method according to claim 1, wherein the thermal energy source has a power output of up to 15 watts.

8. A cancer treatment method using nanoparticle-mediated thermal therapy and photoacoustic imaging, the method comprising the steps of:

administering a plurality of nanoparticles to tissue at a site of a tumor in a patient, a first subset of the plurality of nanoparticles administered to the tissue at the site of the tumor in the patient comprising gold nanoparticles;

heating the tissue and at least some of the plurality of nanoparticles at the site of the tumor in a plurality of different heating stages using a thermal energy source so as to generate photoacoustic signals, damage one or more tumor cell membranes, and release antigenic material in vivo that activates and stimulates an immunogenic response of the patient at the site of the tumor and systemically, the thermal energy source operating near an absorption peak of the gold nanoparticles;

performing photoacoustic imaging with a photoacoustic imaging unit so as to acquire the photoacoustic signals; and determining, by using the photoacoustic imaging unit, a temperature of the heated tissue at the site of the tumor from the photoacoustic signals;

wherein the step of heating the tissue and the at least some of the plurality of nanoparticles further comprises heating at least some of the gold nanoparticles at the site of the tumor, the heating of the gold nanoparticles resulting in an increased temperature rise at the site of the tumor that is five to seven times greater than a temperature rise achieved without the administration of gold nanoparticles;

wherein the plurality of different heating stages comprise a first heating stage at a first predetermined temperature for a first duration of time, a second heating stage at a second predetermined temperature for a second duration of time, and a third heating stage at a third predetermined temperature for a third duration of time; and wherein the second predetermined temperature is greater than the first and third predetermined temperatures, and the second duration of time is less than the first and third durations of time.

9. The cancer treatment method according to claim 8, wherein a second subset of the plurality of nanoparticles administered to the tissue at the site of the tumor in the patient comprises liposomes containing an anti-tumor medication.

10. The cancer treatment method according to claim 9, wherein the anti-tumor medication comprises doxorubicin.

* * * * *